United States Patent
Wrigglesworth et al.

(10) Patent No.: US 11,419,586 B2
(45) Date of Patent: Aug. 23, 2022

(54) SAMPLING DEVICE WITH EJECTABLE COMPARTMENT

(71) Applicant: Mars, Incorporated, McLean, VA (US)

(72) Inventors: David Wrigglesworth, Waltham-on-the-Wolds (GB); William James Bradley, Cambridgeshire (GB)

(73) Assignee: Mars, Incorporated, McLean, VA (US)

( * ) Notice: Subject to any disclaimer, the term of this patent is extended or adjusted under 35 U.S.C. 154(b) by 516 days.

(21) Appl. No.: 15/511,149

(22) PCT Filed: Sep. 11, 2015

(86) PCT No.: PCT/GB2015/052647
§ 371 (c)(1),
(2) Date: Mar. 14, 2017

(87) PCT Pub. No.: WO2016/042301
PCT Pub. Date: Mar. 24, 2016

(65) Prior Publication Data
US 2017/0252017 A1 Sep. 7, 2017

(30) Foreign Application Priority Data

Sep. 17, 2014 (GB) .................................... 1416453
Sep. 17, 2014 (GB) .................................... 1416454

(51) Int. Cl.
*A61B 10/00* (2006.01)
*A61B 5/07* (2006.01)
(Continued)

(52) U.S. Cl.
CPC ........ *A61B 10/0045* (2013.01); *A61B 5/0084* (2013.01); *A61B 5/01* (2013.01);
(Continued)

(58) Field of Classification Search
CPC ............ A61B 10/0045; A61B 10/0038; A61B 5/0084; A61B 5/01; A61B 5/073;
(Continued)

(56) References Cited

U.S. PATENT DOCUMENTS 3,118,439 A 1/1964 Perrenoud
3,485,235 A 12/1969 Felson
(Continued)

FOREIGN PATENT DOCUMENTS

CN 1454571 A 11/2003
CN 104023740 A 9/2014
(Continued)

OTHER PUBLICATIONS

Eddington, et al., "Flow Control with Hydrogels", Science Direct, Advanced Drug Delivery Reviews, 56 (2004), p. 199-210, Accepted: Aug. 20, 2003.
(Continued)

*Primary Examiner* — Tse W Chen
*Assistant Examiner* — Avery M Foley
(74) *Attorney, Agent, or Firm* — Morrison & Foerster LLP

(57) ABSTRACT

The present invention relates to a sampling device 100. The sampling device 100 comprises a separate compartment 110 that is ejected creating an increased space or volume for a sample to be stored. The sampling device 100 of the present invention is suitable for collecting a sample in an aquaculture environment, enclosed system or in the gastrointestinal tract of a human or an animal. The invention also relates to a method of orally administering the device 100 to an animal and recovering the device 100 and/or separate compartment 110 to carry out analysis on the collected sample for diagnosing the health of the gastrointestinal tract and determining nutrient absorption and digestibility.

18 Claims, 16 Drawing Sheets

(51) Int. Cl.
  *A61B 5/01* (2006.01)
  *A61B 5/145* (2006.01)
  *A61B 5/00* (2006.01)

(52) U.S. Cl.
  CPC .......... *A61B 5/073* (2013.01); *A61B 5/14539* (2013.01); *A61B 5/14546* (2013.01); *A61B 5/7285* (2013.01); *A61B 2010/0061* (2013.01); *A61B 2503/40* (2013.01); *A61B 2562/0247* (2013.01); *A61B 2562/166* (2013.01)

(58) Field of Classification Search
  CPC ............ A61B 5/14539; A61B 5/14546; A61B 5/6861; A61B 5/6873; A61B 5/6871; A61B 5/7285; A61B 5/036; A61B 2010/0061; A61B 2562/0247; A61B 2562/166; A61B 5/42; A61B 5/042; A61B 2503/40; A01K 29/005; G01N 1/08
  See application file for complete search history.

(56) References Cited

U.S. PATENT DOCUMENTS

| | | | |
|---|---|---|---|
| 4,186,730 A | | 2/1980 | Bucalo |
| 4,239,040 A * | | 12/1980 | Hosoya ................ A61B 10/02 600/582 |
| 4,481,952 A * | | 11/1984 | Pawelec ................ A61B 10/00 600/582 |
| 5,395,366 A * | | 3/1995 | D'Andrea ............ A61B 5/0031 604/114 |
| 5,443,459 A * | | 8/1995 | Wong ................ A61K 9/0004 604/892.1 |
| 5,971,942 A | | 10/1999 | Gu et al. |
| 6,564,087 B1 * | | 5/2003 | Pitris ................ A61B 1/00172 600/478 |
| 6,632,216 B2 | | 10/2003 | Houzego et al. |
| 7,160,258 B2 | | 1/2007 | Imran et al. |
| 7,611,480 B2 | | 11/2009 | Levy |
| 7,717,862 B2 | | 5/2010 | Stoltz et al. |
| 8,394,034 B2 | | 3/2013 | Iddan et al. |
| 8,444,572 B2 | | 5/2013 | Tanaka |
| 8,562,589 B2 | | 10/2013 | Imran |
| 8,588,887 B2 | | 11/2013 | Arneson et al. |
| 8,636,648 B2 | | 1/2014 | Gazdzinski |
| 8,870,767 B2 | | 10/2014 | Bulitta et al. |
| 9,119,554 B2 | | 9/2015 | Zdeblick et al. |
| 10,172,598 B2 | | 1/2019 | Amoako-Tuffour et al. |
| 2002/0198470 A1 * | | 12/2002 | Imran ................ A61B 1/00082 600/587 |
| 2004/0267240 A1 | | 12/2004 | Gross et al. |
| 2006/0069317 A1 | | 3/2006 | Horn et al. |
| 2006/0246510 A1 | | 11/2006 | Densham |
| 2007/0161928 A1 | | 7/2007 | Sprenkels et al. |
| 2008/0146871 A1 | | 6/2008 | Arneson et al. |
| 2008/0208077 A1 * | | 8/2008 | Iddan ................ A61B 1/041 600/582 |
| 2012/0203084 A1 | | 8/2012 | Li et al. |
| 2014/0287966 A1 | | 9/2014 | Gray et al. |
| 2015/0011874 A1 | | 1/2015 | Amoako-Tuffour et al. |
| 2016/0038086 A1 | | 2/2016 | Wrigglesworth et al. |
| 2017/0252016 A1 | | 9/2017 | Wrigglesworth et al. |
| 2017/0252018 A1 | | 9/2017 | Wrigglesworth et al. |

FOREIGN PATENT DOCUMENTS

| | | |
|---|---|---|
| DE | 19801573 | 7/1999 |
| JP | S5149588 A | 4/1976 |
| JP | 52131678 | 11/1977 |
| JP | S5353183 A | 5/1978 |
| JP | S5376584 A | 7/1978 |
| JP | S53076584 | 7/1978 |
| JP | H04176443 A | 6/1992 |
| JP | H10_192262 A | 7/1998 |
| JP | 2002-298127 A | 10/2002 |
| JP | 2008-500126 A | 1/2008 |
| JP | 2013-56167 A | 3/2013 |
| RU | 2012-116467 A | 11/2013 |
| WO | 02102243 A1 | 12/2002 |
| WO | 2005024436 A1 | 3/2005 |
| WO | 2005046485 | 5/2005 |
| WO | 2013/120184 A1 | 8/2013 |
| WO | 2014/140334 A1 | 9/2014 |

OTHER PUBLICATIONS

Hammond et al., "A system-on-chip digital pH meter for use in a wireless diagnostic capsule," IEEE Transaction on Biomedical Engineering, 2005, 52(4):687-694.

Johannessen et al., "Implementation of multichannel sensors for remote biomedical measurements in a microsystems format," IEEE Transaction on Biomedical Engineering, vol. 51, pp. 525-535, Mar. 2004.

Twomey et al., "Swalloable capsult technology: Current perspectives and future directions," Endoscopy 2009, 41(4):357-362.

International Search Report and Written Opinion dated Dec. 14, 2015, directed to International Application No. PCT/GB2015/052647; 8 pages.

International Search Report and Written Opinion dated Dec. 15, 2015, directed to International Application No. PCT/GB2015/052648; 8 pages.

Search Report dated Jun. 9, 2019, directed to CN Application No. 201580062359.4; 1 page.

Search Report dated Mar. 26, 2019, directed to JP Application No. 2017-514671; 27 pages.

Search Report dated May 28, 2019, directed to CN Application No. 201580062406.5; 1 page.

* cited by examiner

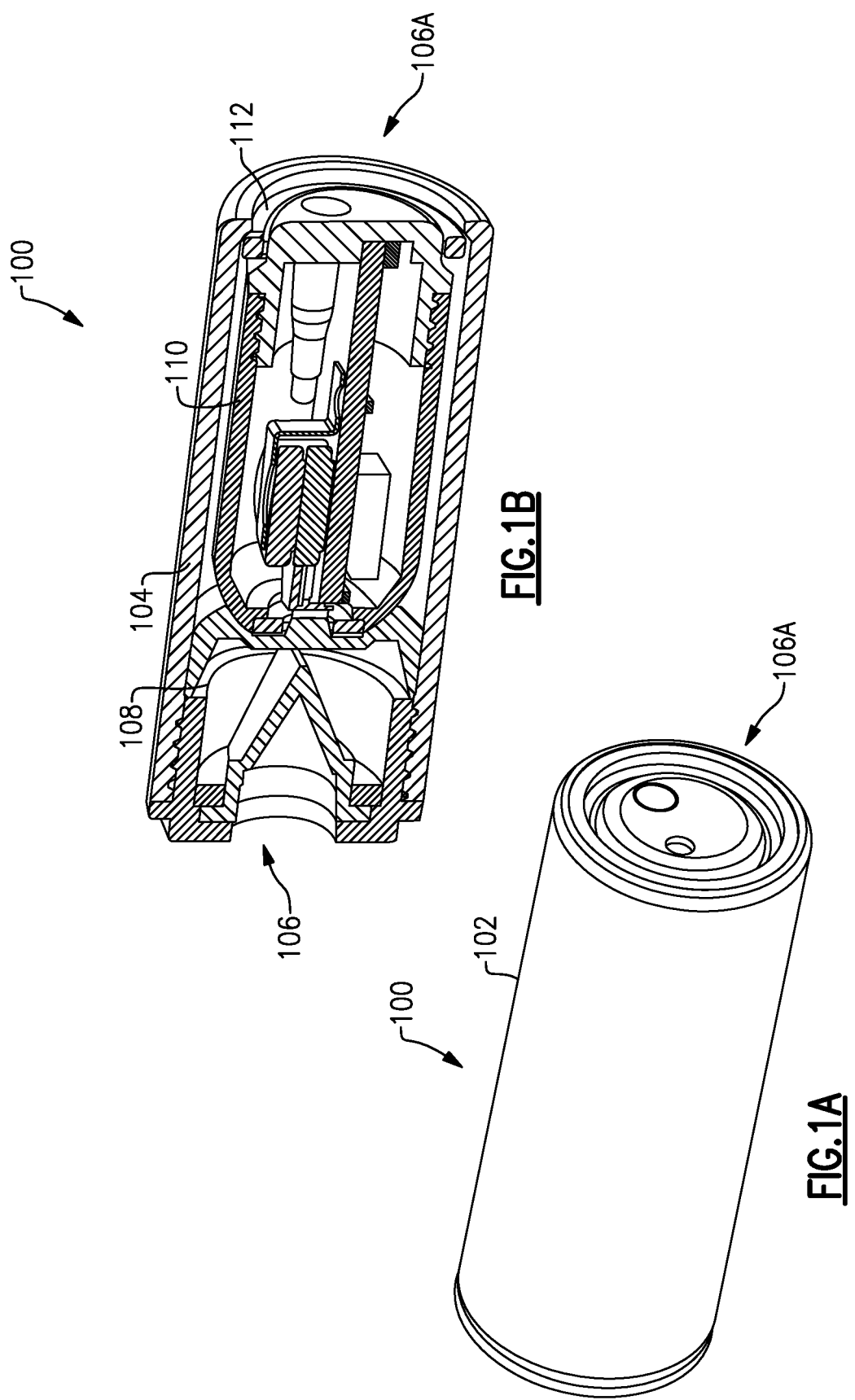

SAMPLING DEVICE WITH EJECTABLE COMPARTMENT

CROSS REFERENCE TO RELATED APPLICATIONS

This application is a national stage application, filed under 35 U.S.C. § 371, of International Application No. PCT/GB2015/052647, filed Sep. 11, 2015, which claims priority to GB Application Serial No. 1416453.7, filed on Sep. 17, 2014, entitled "DEVICE" and GB 1416454.5, filed on Sep. 17, 2014, entitled "DEVICE," the entire contents of which are incorporated herein by reference for any and all purposes.

FIELD

The present invention relates to a sampling device. The sampling device comprises a separate compartment that is ejected creating an increased space or volume for a sample to be stored. The sampling device of the present invention is suitable for collecting a sample in an aquaculture environment, enclosed system or in the gastrointestinal tract of a human or an animal. The invention also relates to a method of orally administering the device to an animal and recovering the device to carry out analysis on the collected sample for diagnosing the health of the gastrointestinal tract and determining nutrient absorption and digestibility.

BACKGROUND

The ability to directly sample substances within the gastrointestinal tract of an animal is a key enabling technology for diagnosing the health of the gastrointestinal tract; understanding ileal digestion, fermentation in the colon and for investigating the relationship between specific dietary components and the biological, chemical and physio-chemical properties in the gastrointestinal tract of humans and/or animals. This includes nutrient absorption, drug metabolism, microorganism distribution, immunological status and so on.

Analyzing a sample of substance, such as a gas, a solid particle or a liquid from the gastrointestinal tract of an animal, can provide information on the pH, enzyme activity, microbial load/content and molecular composition of the sampled material including nutrient load and degree of processing information enabling the assessment of health status and diagnosis of diseases, and in particular diseases of the gastrointestinal tract can also be obtained through determination of immune factors or general immunological status, characterisation of the microflora present and presence/absence of microbial pathogens or microbes associated with health.

Early detection, identification of and location of abnormal conditions can be critical for definitive diagnosis and/or treating various pathologies. Particular control over the site of digesta sampling is also vital to the understanding of health and disease since conditions are generally site specific for example relating to either the stomach, ileum or colon as opposed to affecting the entire gastrointestinal tract. Site specific sample acquisition is also of use for understanding dietary impact and nutrition, for example, ilea processing is an important factor in diet design since the efficiency of digestion and absorption within the small intestine impacts on the luminal contents present in the distal portion of the gastrointestinal tract. Fermentation by the intestinal flora within the colon is dependent on the luminal contents reaching the colon and hence factors such as incomplete protein digestion have been associated with the formation of toxic compounds, including ammonia, di-hydrogen sulphide, in-doles and phenols, which in turn have been shown to increase the risk of colon cancer in humans. In the design of diets for "production animals", it is also important to enhance the efficiency of nutrient availability in foodstuffs and the environmental impact of waste products from the animal.

Whilst total apparent digestibility (as measured by the percentage of ingested nutrient that is recovered in the faeces) is a key measure, this methodology has a number of shortcomings, due to the contamination of faeces with metabolic waste products and substances of non-dietary origin. Ileal digestibility is therefore a more appropriate measure of nutrient delivery. Furthermore, the outflow of the terminal ileum into the caecum can be considered as the substrate upon which the hind gut microflora act. The colonic digesta or luminal contents may therefore provide a predictor or allow assessment of the nutrients available for fermentation by the resident gastrointestinal microflora. Consequently, the ability to measure a broad range of chemical (e.g. protein, carbohydrates, fats, non-starch polysaccharides, micronutrients, anti-nutritional factors), biological and physio-chemical (e.g. viscosity) properties from within the ileal and colonic digesta represents a significant development that may in turn enable a step-change in our understanding of the effects of specific dietary components on digestive processes and its products. Such digestion products may include faecal characteristics such as faeces quality and consistency and intestinal gas or flatulence. The development of these enabling technologies may also, enable diagnosis and research into gastrointestinal diseases.

There is an ongoing need to improve known sampling devices, such that a larger volume of sample may be acquired, and sampling of liquids ranging in viscosity as well as solid samples can be acquired.

BRIEF DESCRIPTION

A sampling device is provided herein. The sampling device allows a greater range of analytical tests to be carried out on the sample and enhance the range of samples for acquisition. Furthermore, the sampling device has the capability to alter the point within the gastrointestinal tract at which the sample is captured, thereby allowing investigation of the changes in factors involved in digestion (pH, enzymes emulsifying agents etc.), dietary processing; nutrient absorption; microbial populations; immune factors and digesta viscosity throughout the length of the gastrointestinal lumen. Sampling may therefore proceed within the stomach, ileum, colon and caecum allowing sampling site to be adjusted based on the nature of the sample required.

The device of the present invention is simple, inexpensive, reliable and easy to use, without the need for constant monitoring and may be reusable. The device of the present invention can be recovered and the sample easily extracted and analysed using a variety of biological, chemical and physical assays. Both liquid and solid substances can be sampled by the device of the present invention.

The device of the invention is able to log a change in the environment over a long period of time, e.g. for 24 hours. In particular, the change in the environment along the gastrointestinal tract of an animal. The device of the invention is able to download the data stored to a computer and be easily reprogrammed to be reused. The device of the invention is able to detect and log the time pH and/or temperature at which the sample is obtained.

In particular, the device of the invention is able to collect a large amount of sample as a result of its separate compartment being ejected creating an increased volume or space for a sample to be collected and stored.

In a first aspect, a sampling device is provided. The sampling device comprises a housing, the housing comprising a chamber, at least an opening, an actuation means and a separate compartment. The separate compartment is releasably retained within the housing by a retention means and is ejectable from the housing. The device may be reuseable.

The at least one opening may be an inlet or an outlet and may comprise a one-way valve.

The actuation means may comprise a plunger, a spring, or a combination of these. The actuation means is coupled at one end of the housing of the sampling device and the separate compartment is releasably retained by a retention means within the housing at the opposing end of the sampling device.

The actuation means causes an internal substance to be drawn in through the opening into the chamber and also pushes the separate compartment through the interior of the housing until the separate compartment is ejected therefrom. The actuation means may be prevented from being ejected from the housing by a stopper, e.g., a lip, pin, lug, or protrusion, at the end of the housing from which the separate compartment is ejected from the sampling device. Increased space or volume for receiving and storing a sample within the chamber of the sampling device is provided by the ejection of the separate compartment out of the housing by the actuation means.

The retention means comprises a material that reacts to changes in the external environment of the device, e.g., the material may react to pH, temperature, light, moisture, solute concentration or enzymatic degradation. The material of the retention means may be degradable, digestible or soluble. The retention means may both react to changes in the environment external to the device, and also be degradable, digestible or soluble.

The retention means may also be activated by a trigger such as a piezoelectric means, a shape memory alloy, a muscle wire, or a sacrificial fuse. The trigger, in turn, may be activated, and/or the retention means released in response to, a change in pH, a change in temperature, a change in moisture, a change in solute concentration, a change in enzyme concentration or a change in light and/or is activated at a pre-determined time and/or at a pre-determined pH and/or at a pre-determined temperature and/or pre-determined moisture level and/or pre-determined solute concentration and/or pre-determined enzyme activity or concentration.

The retention means and/or the trigger means may also be activated automatically, pre-programmed to activate at a specific time or in response to a specific condition and/or activated remotely. In some embodiments, the retention means is a bayonet mount that is activated by a trigger means. In others, the retention means is a rubber O-ring washer that is activated by a trigger means.

The retention means may further comprise an interlocking mechanism between the housing and the separate compartment and may be fastened and/or released by rotatory, radial or linear motion or means. One example of a suitable rotary interlocking mechanism is a bayonet. One example of a suitable radial interlocking mechanism is a rubber O-ring. One example of a linear interlocking mechanism is a pin that pushes the separate compartment into place.

After the actuation means and/or retention means is activated, the separate compartment is at least partially released and at least partly disengaged from the actuating means. Desirably, the separate compartment is completely ejected from the housing of the sampling device, so that the device and the separate compartment may be recovered separately.

The separate compartment comprises at least a battery, a sensor and a microprocessor. The sensor may be a pH sensor, a temperature sensor, or a combination of these. The separate compartment may further comprise a switch, such as a pressure switch, that is adapted to record the timing at which the separate compartment is ejected from the housing of the sampling device.

In a second aspect, a method of obtaining a sample from the gastrointestinal tract of an animal is provided. The method comprises orally administering the device as claimed in any one of the previous clauses to the animal and recovering the device. The separate compartment may also desirably be recovered. The sample within the device may then be tested as desired. The animal may be a human, a companion animal, such as a horse, dog or cat, or a farm animal or a production animal such as a horse, cow, sheep and/or chicken.

BRIEF DESCRIPTION OF THE DRAWINGS

Reference is made to the attached Figures in which:

FIGS. 1A and B are perspective full and cross-sectional views, respectively of one embodiment of the sampling device;

DETAILED DESCRIPTION

Figure 2A:
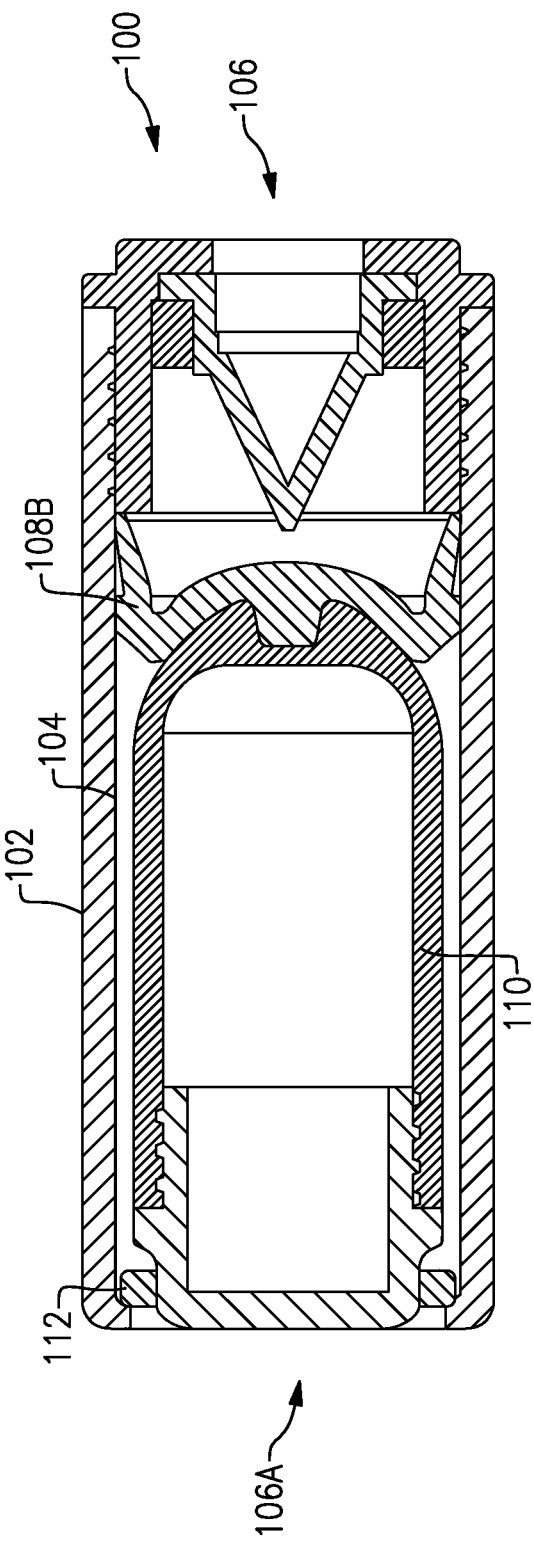
FIGS. 2A and 2B are schematic cross-sectional views of additional embodiments of the sampling device.

The present sampling device allows a greater range of analytical tests to be carried out on the sample and enhance the range of samples for acquisition. Furthermore, the sampling device has the capability to alter the point within the gastrointestinal tract at which the sample is captured, thereby allowing investigation of the changes in factors involved in digestion (pH, enzymes emulsifying agents etc.), dietary processing; nutrient absorption; microbial populations; immune factors and digesta viscosity throughout the length of the gastrointestinal lumen. Sampling may therefore proceed within the stomach, ileum, colon and caecum allowing sampling site to be adjusted based on the nature of the sample required.

The device of the present invention is simple, inexpensive, reliable and easy to use, without the need for constant monitoring and may be reusable. The device of the present invention can be recovered and the sample easily extracted and analysed using a variety of biological, chemical and physical assays. Both liquid and solid substances can be sampled by the device of the present invention.

The device of the invention is able to log a change in the environment over a long period of time, e.g. for 24 hours. In particular, the change in the environment along the gastrointestinal tract of an animal. The device of the invention is able to download the data stored to a computer and be easily reprogrammed to be reused. The device of the invention is able to detect and log the time pH and/or temperature at which the sample is obtained.

In particular, the device of the invention is able to collect a large amount of sample as a result of its separate compartment being ejected creating an increased volume or space for a sample to be collected and stored.

In a first aspect of the invention there is provided a sampling device 100. As shown in FIGS. 1A and 1B, the sampling device 100 comprises a housing 102, wherein the housing 102 comprises a chamber 104, at least an opening 106, an actuation means 108 and a separate compartment 110, wherein the separate compartment 110 is releasably retained within the housing 102, the actuation means 108 enables an internal substance to be drawn in through the opening 106 into the chamber 104 and simultaneously pushes the separate compartment 110 along the housing 102 until the separate compartment 110 is ejected from the housing 102 of the sampling device 100, thereby creating an increased space or volume for receiving and storing a sample within the chamber 104 of the sampling device 100.

In some embodiments, the sampling device 100 can be used for sampling any form of closed system, such as fish tanks, processing tanks, bioprocessing, various agricultural systems or any system where human/physical intervention is beneficial and/or industrial or factory pipes.

In particular embodiments, the sampling device 100 of the invention is for sampling internal substance from within the gastrointestinal tract of an animal.

The terms "sample", "substance" and "internal substance" are used interchangeably and refers to any liquid, solid, particle or gas, which can be sampled by the device 100, more specifically these terms may also be referred to as digesta or luminal contents or digestion products when referring to sampling within the gastrointestinal tract of an animal. Liquid can for example be found in the stomach, small and large intestine. Such liquids may contain solids or species in solution (or suspensions) such as dietary components, drugs, food components; digestion products, microbial metabolites, gases, such as oxygen, hydrogen, carbon dioxide, methane, hydrogen sulfide, etc. can also be found.

In particular, the device 100 is designed to withstand any pressure (such as chewing) and/or change in environment. In particular, the device 100 is designed to travel along the gastrointestinal tract of an animal. The device 100 must be able to withstand peristalsis of the gastrointestinal tract, as well as the chemical and mechanical environment of the gastrointestinal tract.

Different materials may be used for each different component of the sampling device 100. In particular, the material used determines the texture and/or hardness of the device 100. The materials can be hard, soft, smooth and/or malleable and the preference of the material used is dependent on its use.

Typically, the device 100 can be made of any non-digestible, non-biodegradable, non-immunogenic, non-bioreactive or impermeable material. In particular, the material used to make the device 100 can be any biologically inert polymeric materials, such as acrylonitrile butadiene styrene (ABS) polytetrafluoroethylene (PTFE), polyethylene, polyvinyl chloride, acrylics and the like, ceramics or metals, for example stainless steel, preferably smooth surfaced for ease of ingestion and transit and with at least one radio opaque surface or inclusion such that it can be observed radiographically if required.

Thermoplastic materials can be used, such as polycarbonates, acrylonitrile butadiene styrene (ABS), High-density polyethylene (HDPE), Low-density polyethylene (LDPE), Polyether ether ketone (PEEK) or Polypropylene (PP).

Preferably, the external surface of the device 100 is made of polycarbonate. The polycarbonate may be translucent to aid in the visual assessment of the contained sample. Other components are preferably made from polytetrafluoroethylene (PTFE). In particular, PTFE may be used for internal components of the device 100 where the flexible nature of this material allows a seal to be formed between two adjacent surfaces.

All materials used in the sampling device 100 are inert and safe for food and/or medical use.

In some embodiments, the device 100 can be in a shape of a capsule or a pill. The capsule can be cylindrical with rounded, conical or flattened ends. The device 100 can be partially spherical in shape.

The sampling device 100, and in particular the different components of the sampling device 100, are fabricated with conventional tools and/or methods known in the art. In particular, the sampling device 100 and components thereof may be fabricated using additive techniques such as 3D printing or by reductive techniques such as CNC machining known to the art.

In particular, the device 100 is preferably suitable for swallowing and for an animal to ingest. Capsules known in the art have dimensions of 26 mm to 30 mm×11 mm to 15 mm (length×width).

The particular advantage of the present invention is that although the sampling device 100 may have similar dimensions as those known in the art, a separate compartment 110 within the sampling device 100 is ejected creating an increased volume or space for a sample to be received and/or stored. Depending on the animal, size, breed and/or species, the device 100 will vary in size as described herein. The dimensions of the device 100 can range from about 10 mm to 70 mm in length to 3 mm to 25 mm in width. In particular, the dimensions of the device 100 may be about 10-15 mm and about 3-7 mm, about 15-25 mm×about 7-12 mm, about 20-30 mm×about 10-17 mm, about 30-40 mm×about 15-20 mm, about 10-20 mm×about 3-20 mm, about 35-65 mm×about 7-23 mm, or about 40-70 mm×about 10-25 mm and/or any combination thereof.

Depending on the size of the capsule used, the device 100 of the invention is capable of obtaining a sample volume from about 0.11 ml to about 20 ml. In particular, the sample volume can be about 0.11 ml to 3 ml, about 1 ml to 5 ml, about 3 ml to 7 ml, about 7 ml to 13 ml, about 10 ml to 15 ml, about 13 ml to 17 ml or about 15 ml to 20 ml and/or any combinations thereof. In a particular example of the invention, the device 100 may have an internal volume of 1.53 cm$^3$ and may be capable of obtaining and storing a sample volume of 1.3 ml, which is 85% of the available internal volume.

The device 100 can most preferably have dimensions of about 20 to 25 mm×about 9 to 12 mm (length×width).

The device 100 is of a modular design in that it comprises one or more components. In particular, the device 100 is assembled from one or more components. One component may comprise an actuation means 108 and an opening 106. Another component may comprise a housing 102. Another component may comprise a stand-alone separate compartment 110.

The different components of the sampling device 100 may be formed separately and easily assembled together to form the sampling device 100 and/or separate parts of the sampling device 100.

In some embodiments, the sampling device 100 can comprise two halves connected at least to one another by one or more elements and/or the housing 102.

In some aspects of the invention the sampling device 100 comprises a housing 102, wherein the housing 102 comprises a chamber 104, at least an opening 106, an actuation means 108 and a separate compartment 110, wherein the separate compartment 110 is releasably retained within the housing 102 by a retention means 112 and wherein the actuation means 108 enables an internal substance to be drawn in through the opening 106 into the chamber 104 and simultaneously pushes the separate compartment 110 along the housing 102 until said separate compartment 110 is ejected from the housing 102 of the sampling device 100, thereby creating an increased space or volume for receiving and storing a sample within the chamber 104 of the sampling device 100.

In yet other aspects of the invention, the sampling device 100 comprises a housing 102, wherein the housing 102 comprises a chamber 104, at least an opening 106, an actuation means 108 and a separate compartment 110, wherein the separate compartment 110 is releasably retained within the housing 102 by a retention means 112 that is activated by a trigger means 114 (shown in FIGS. 5B, 6, and 7), wherein the actuation means 108 enables an internal substance to be drawn in through the opening 106 into the chamber 104 and simultaneously pushes the separate compartment 110 along the housing 102 until said separate compartment 110 is ejected from the housing 102 of the sampling device 100, thereby creating an increased space or volume for receiving and storing a sample within the chamber 104 of the sampling device 100.

In another aspect of the invention, there is provided a sampling device 100 comprising a housing 102, wherein the housing 102 comprises a chamber 104, at least an opening 106, an actuation means 108 and a separate compartment 110, wherein the separate compartment 110 is releasably retained within the housing 102 by a retention means 112 that is a material that reacts to changes in the external environment of the device 100 and wherein the actuation means 108 enables an internal substance to be drawn in through said opening 106 into said chamber and simultaneously pushes the separate compartment 110 along housing 102 until said separate compartment 110 is ejected from the housing 102 of the sampling device 100, thereby creating an increased space or volume for receiving and storing said sample within the chamber 104 of the sampling device 100.

In another aspect of the invention, there is provided a sampling device housing 102, wherein the housing 102 comprises a chamber 104, at least an opening 106, an actuation means 108 and a separate compartment 110, wherein the separate compartment 110 is releasably retained within the housing 102 by a retention means 112, wherein the retention means 112 is an interlocking mechanism between the housing 102 and the separate compartment 110 and wherein the actuation means 108 enables an internal substance to be drawn in through the opening 106 into the chamber 104 and simultaneously pushes the separate compartment 110 along the housing 102 until the separate compartment 110 is ejected from the housing 102 of the sampling device 100, thereby creating an increased space or volume for receiving and storing a sample within the chamber 104 of the sampling device 100. Various embodiments of interlocking mechanisms are shown in FIGS. 8A-8L.

In yet another aspect of the invention, there is provided a sampling device 100 comprising a housing 102, wherein the housing 102 comprises a chamber 104, at least an opening 106, an actuation means 108 and a separate compartment 110, wherein the separate compartment 110 is releasably retained within the housing 102 by a retention means 112 and wherein the actuation means 108 enables an internal substance to be drawn in through the opening 106 into the chamber 104 and simultaneously pushes the separate compartment 110 along the housing 102 until the separate compartment 110 is ejected from the housing 102 of the sampling device 100, thereby creating an increased space or volume for receiving and storing a sample within the chamber 104 of the sampling device 100, wherein the actuation means 108 is tethered 116 to a closure means 118 and wherein the movement of the actuation means 108 results in the closure means 118 blocking the opening 106.

As shown in FIG. 2A, the sampling device 100 comprises a housing 102. The housing 102 comprises a chamber 104, at least an opening 106 and a separate compartment 110. In particular, the housing 102 is an enclosure, which holds an actuation means 108 and the separate compartment 110 within the sampling device 100.

In some embodiments, the housing 102 can be made from polycarbonate.

In particular, the sampling device 100 of the invention is re-usable. In particular, the separate component 110 can be unscrewed and reused multiple times. The entire device 100 can be re-used. In certain embodiments of the invention, the material that reacts with the external environment of the device 110, the battery(s) 120, and/or the trigger means 114 may require replacing, e.g. Eudragit washer, wax washer, fuse, or the battery.

The housing 102 of the sampling device of the invention may have one or more openings.

In particular, the sampling device 100 has at least one opening 106. The opening 106 may be an inlet 106 and/or an outlet 106A. The opening 106 may be an aperture or a hole at one or either end of the housing 102. In particular embodiments, the opening 106 is an inlet, which allows sample into the housing 102 of the sampling device 100, preferably into the chamber 104. Alternatively, the opening 106 can be an outlet 106A which allows the separate compartment 110 to be ejected from the housing 102 of the sampling device 100. In particular, the housing 102 may have two openings, one on each end of the housing 102 on opposing ends of the sampling device 100 (an inlet 106 and an outlet 106A).

In some embodiments, the inlet opening 106 can comprise a valve. The valve can be any valve known in the art and will depend on the use of the sampling device 100. The valve includes an aperture. The valve can be made from rubber or synthetic elastomer. Preferably, the valve is made of elastomer which is resistant to low pressure therefore opening the aperture. In other embodiments, the opening 106 can be an inlet and an outlet 106A. The opening can be a two way valve. Most preferably, the opening 106 is a one-way valve.

In some embodiments, the opening 106 includes an aperture without the valve.

The sampling device 100 comprises an actuation means 108.

In particular, the actuation means 108 is arranged in a first configuration and capable of moving to a second configuration within the housing 102 of the sampling device 100. The first configuration is a compressed state and the second configuration is an expanded state. The actuation means 108 assists in drawing a sample into the housing 102 of the sampling device 100, preferably into the chamber 104.

In particular, the actuation means 108 enables a sample to be drawn in through the opening 106 into the chamber 104 of the housing 102 of the device 100 and simultaneously pushes the separate compartment 110 through the housing 102 until the separate compartment 110 is ejected from the device 100.

An actuation means 108 can be any object or element that is capable of storing internal energy for a period of time within the device 100. In particular, an actuation means 108 can be a system and/or an object capable of putting another object or element into motion and/or action, for example providing the force to move the separate compartment 110 from a retained and compressed state to an uncompressed and ejected state.

The actuation means 108 can include a spring, a chemical reaction (releasing gas and producing pressure), an electronically powered actuator (such as a motor or a pump), compressed air or a vacuum energy store.

The actuation means 108 retains an amount of internal energy, preferably for a pre-determined time in various pre-determined conditions.

The actuation means 108 is held in compression when the separate compartment 110 is in place.

An actuation means 108 may comprise a resilient member. In particular, it may comprise any object that is capable of storing kinetic energy and/or capable of movement. A resilient member may be a spring and/or a plunger/piston.

The actuation means 108 at least comprises a plunger/piston. The actuation means can comprise a plunger/piston 108B and a spring 108A, a plunger/piston 108B and an electronically powered actuator 108C, etc. In some embodiments, the plunger/piston 108B may be moved from the first configuration to the second configuration within the housing 102 of the sampling device 100 by means of a chemical reaction within the housing 102 of the device 100 which releases gas and/or produces pressure.

The movement of the actuation means 108 (e.g. the spring 108A that is coupled to the plunger/piston 108B or the plunger/piston 108B forced along the housing 102 by other means) pushes the separate compartment 110 simultaneously out of the housing 102 of the sampling device 100.

In particular, the actuation means 108 draws up a sample through the opening 106 of the sampling device 100 into the chamber 104 and simultaneously pushes the separate compartment 110 along the length of the housing 102 of the sampling device 100 until the separate compartment 110 is ejected from the housing 102 of the sampling device 100.

In particular embodiments, the actuation means 108 includes a spring 108A.

Typically a spring 108A is an elastic object, such as a coil of wire, which regains its original shape after being compressed or extended and releasing stored energy during the return to the original state. A spring 108A can include any type of spring such as a coil spring, conical spring, a torsion spring, a compression spring, or a wave spring, etc. The spring 108A can be made of any material that is resistant and elastic, such as stainless steel or other metal or alloy.

In a particular embodiment, the spring 108A acts as an actuator 108. The actuator 108 is held in a compressed state by the separate compartment 110. The spring 108A can drive the plunger/piston 108B through the housing 102 (e.g. along the length of the housing 102) pushing the separate compartment 110 out of the housing 102 of the sampling device 100, converting the actuation means 108 from its first compressed configuration to the second expanded configuration. The driving force of the spring 108A creates a short time framed vacuum, as it expands along the housing 102 and/or a capillary action in which the sample is drawn into the housing 102 of the sampling device 100, preferably into the chamber 104 through the opening 106.

When the separate compartment 110 is not in place (i.e. has been ejected from the housing 102 of the sampling device 100), a stopper means at the end of the housing 102 of the sampling device 100 prevents the plunger/piston 108B from exiting the device 100.

The motion of the separate compartment 110 being ejected from the housing 102 of the sampling device 100 is caused by the actuation means 108.

Figure 2B:
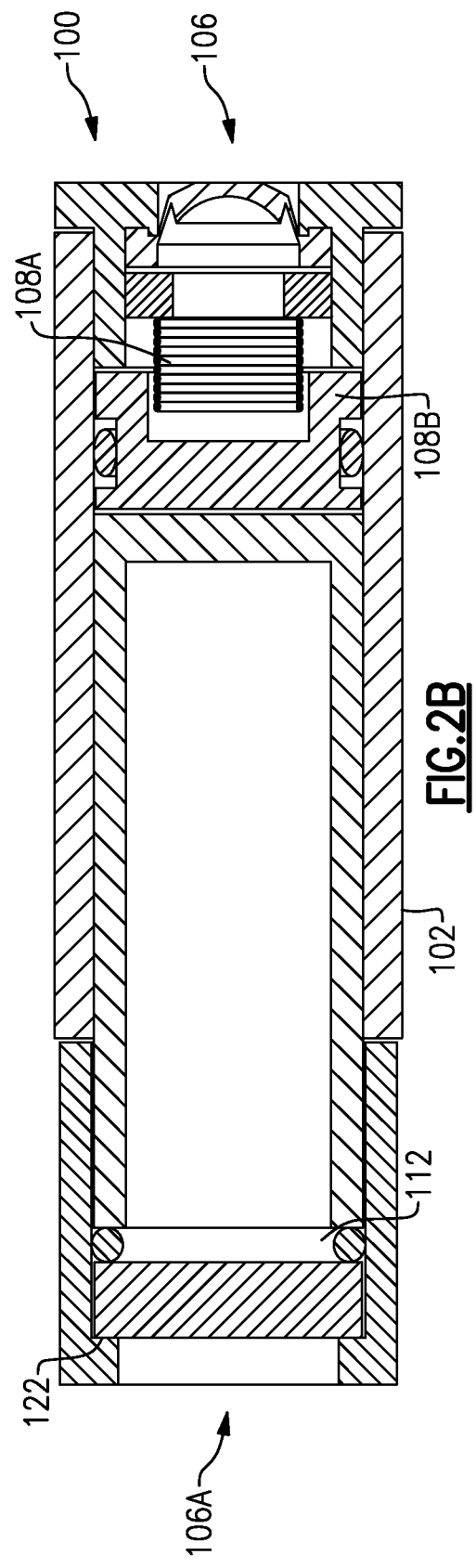
Figure 3:
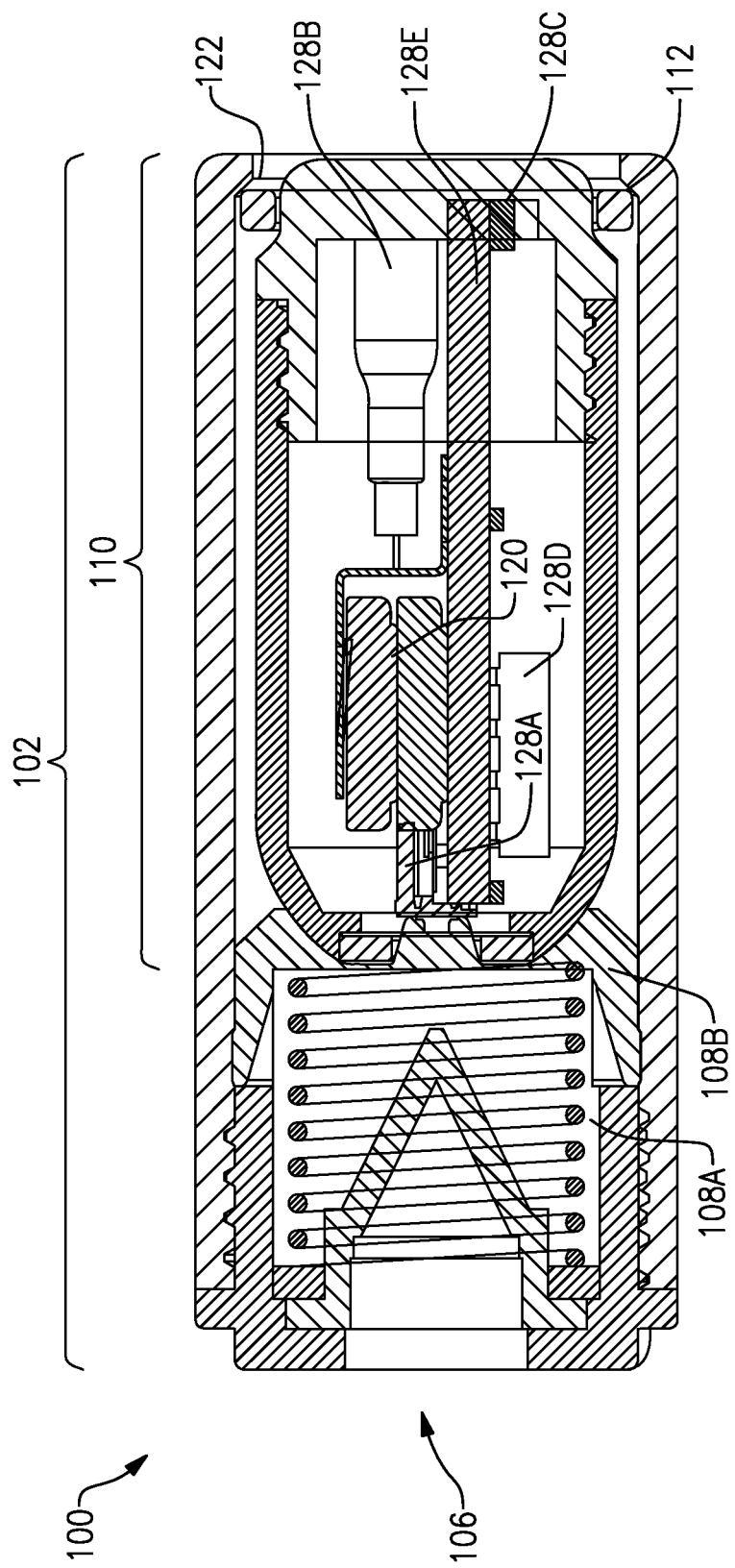
FIG. 3 is a schematic cross sectional view of an embodiment of the sampling device.

Preferably, the actuation means 108 is a spring 108A and a plunger 108B arrangement or a spring 108A and a piston arrangement 108B (as shown in FIG. 2B).

In some embodiments, the actuation means 108 is coupled at one end of the housing of the sampling device 100 and the separate compartment 110 is at least releasably retained by a retention means 112 within the housing 102 at the opposite end of the sampling device 100.

In particular, when the actuation means 108 reaches the opposite end of the housing 102 it is capable of forming a seal, so that the device 100 is sealed.

Figure 4:
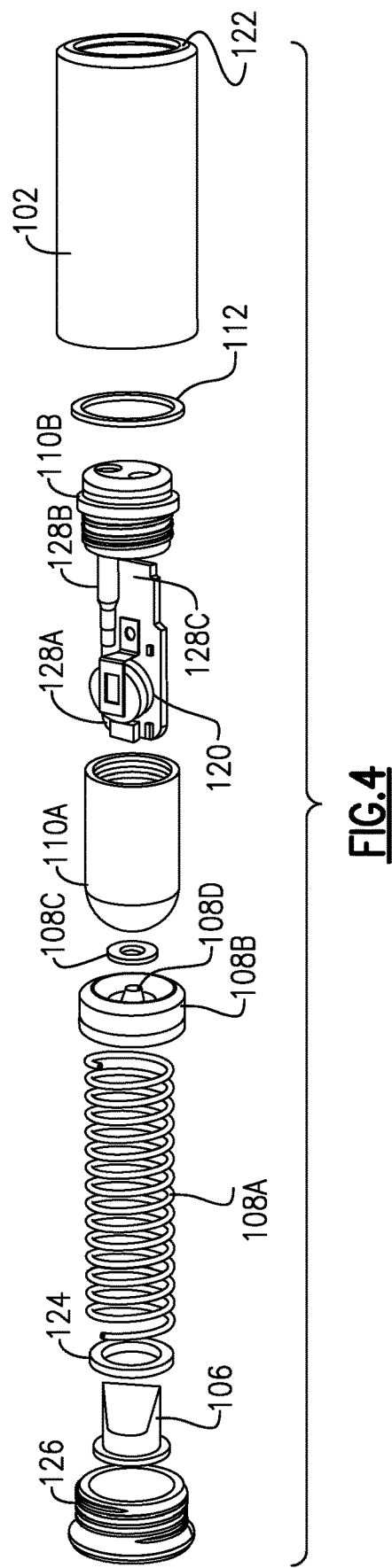
FIG. 4 is an expanded perspective view of the different components of one of the embodiments of the sampling device, separated.

In particular, and as is shown in FIG. 4, the actuation means 108 is coupled to the valve 106. In particular, the actuation means 108 and the valve 106 are coupled in a holder. The holder can be made from any material, in particular from polycarbonate. When coupling the actuation means and the valve into the holder, a retaining ring 124 may be used, such as an O-ring.

The term "coupled" refers to two or more objects which are attached to one another directly or through one or more intermediate elements, or are held adjacent to one another.

In particular, the actuation means 108 and the opening 106 can be connected to provide an individual component of the sampling device 100, which is capable of attaching and/or fixing to the housing 102 of the sampling device 100. Preferably, the actuation means 108 and the opening 106 are coupled together into an individual compartment which screws into one end of the housing of the device 100, via screwcap 126.

The plunger/piston 108B may be made from poly tetrafluoroethylene.

In particular, and as is shown in FIG. 4, the actuation means 108 (e.g. spring 108A and plunger/piston 108B) is adapted with a protrusion 108D that is capable of engaging with the separate compartment 110. The protrusion 108D is positioned centrally to the separate compartment 110, such that the separate compartment 110 travels in a linear manner when being ejected under the force exerted by the actuation means 108. In particular, the protrusion 108D is on the upper surface of the actuation means 108. The protrusion 108D may include a magnet, an inductive coil or a light source.

In particular embodiments of the invention, the sampling device 100 includes a closure means 118.

Figure 7:
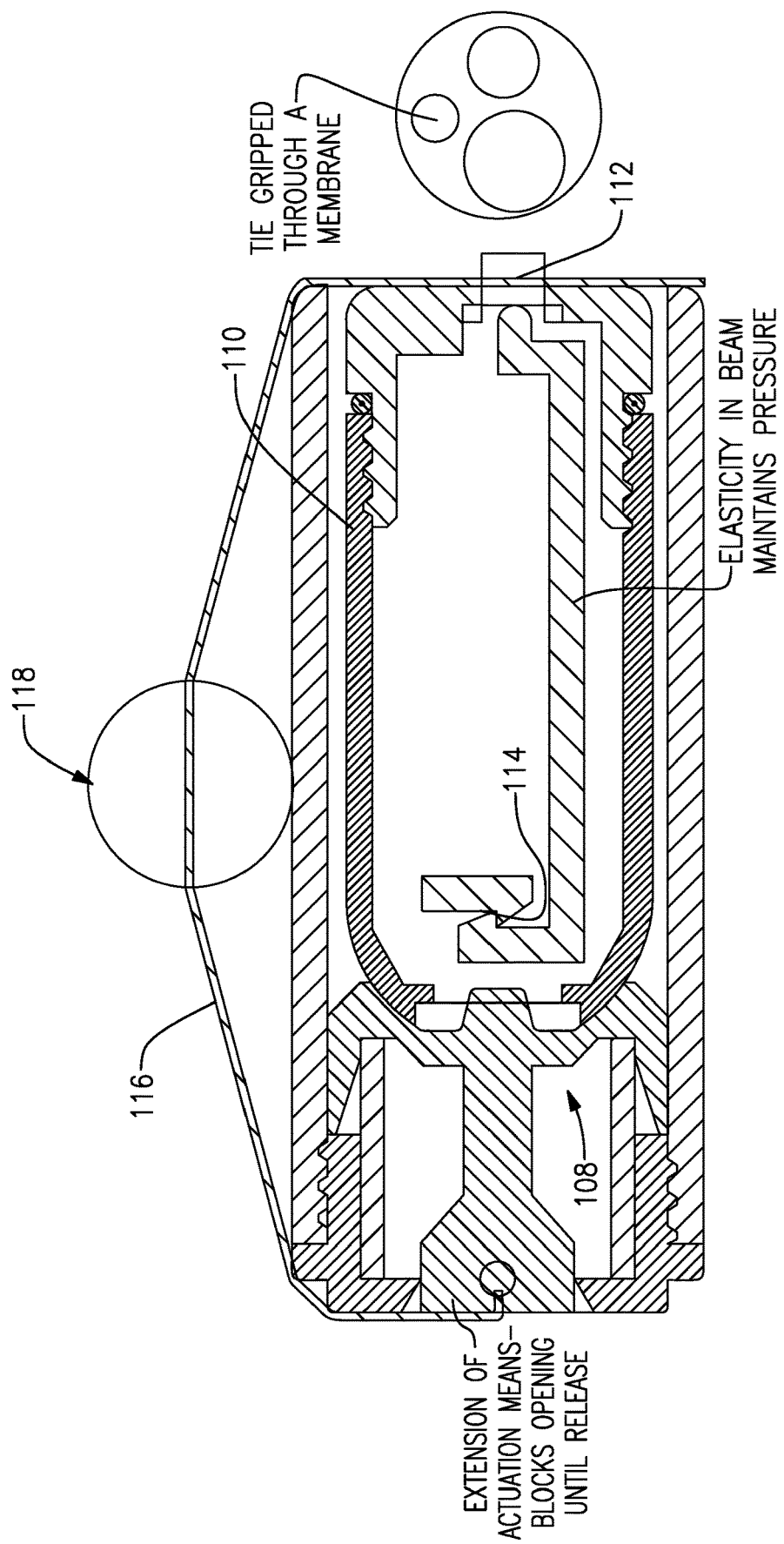
FIG. 7 is a cross-sectional view of a sampling device incorporating another embodiment of a retention means.

A closure means 118 is an object that obstructs an aperture. In particular, the closure means 118 can block any one of the openings 106. The closure means 118 can be any form of element or object that is capable of blocking or plugging the opening 106 of the device 100, such as a ball of thermoplastic material, or similar material thereby forming a seal in the opening 106 of the device 100. The closure means 118 assists in closing the opening 106. The closure means 118 can be a block, ball, lid or other. In particular, and as is shown in FIG. 7, the closure means 118 can be tethered 116 to the actuation means 108. In particular, the closure means 118 can be tethered 116 to the actuation means 108 and the retention means 112.

The term "tether", "tethering" or "tethered" refers to any form of a cord, fixture, or flexible attachment that anchors something movable to another element or a part which can also be moveable or fixed.

In another embodiment, and as is also shown in FIG. 7, the actuation means 108 (e.g. the plunger/piston 108B) is tethered to a closure means 118, which is pulled into tension as the actuation means 108 moves along the housing 102 of the sampling device 100. In particular, as the actuation means 108 is moved, the tether is tensed and drawn into the housing 102 of the sampling device 100, until the closure means 118 reaches the opening 106. The closure means 118 can be pulled or pushed into the opening 106, forming a closed device 100. Simultaneously, the actuation means 108 has drawn sample into the chamber 104 of the device 100 and the separate component 102 is ejected. Thereby, the sample is sealed within the device 100.

In particular, the housing 102 of the sampling device 100 includes a stopper means 122.

The stopper means 122 prevents the actuation means 108 (e.g. plunger/piston 108B) from ejecting from the housing 102. The stopper means 122 can be any protrusion and/or additional element or object that obstructs or halts another object at a given point. In particular the stopper means 122 is a protrusion that stops the actuation means from exiting the housing. The stopper means 122 can be located at the end of the housing 102 from which the separate compartment 110 is ejected. It functions by stopping the actuation means 108 (e.g. plunger/piston 108B) from being released further and along with the separate compartment 110 that is ejected from the device 100. In particular, the stopper means 122 acts to stop the actuation means 108 from being ejected and thereby seals the device 100.

The stopper means 122 can be a lip, lug, protrusion, or pin.

The sampling device 100 comprises a separate compartment 110, wherein the separate compartment 110 is a stand-alone compartment. The separate compartment 110 can be inserted loosely and/or fitted into the housing 102 of the sampling device 100.

In particular, and as is shown in FIG. 4, the separate compartment 110 is an enclosed compartment, which can be unscrewed at any given time for reusing. The separate compartment 110 is composed of two separate components, a body 110A and a lid or screwcap 110B. The lid 110B is coupled with the associated electronics 128 and a power source (e.g. a battery 120). The lid 110B can screw into the body 110A of the separate compartment 110 and be tightly sealed. In particular, the lid 110B may further comprise an O-ring (not shown).

In particular, the separate compartment 110 is air and water tight.

The interface of the lid 110B and body 110A of the separate compartment 110 may be coated with a food safe silicon grease to aid sealing. The associated electronic components 128 may be encased in Polytetrafluoroethylene (PTFE) tape to prevent contamination with liquid, grease, or other material that may interfere with the correct functioning of the electronic components.

In some embodiments, the sampling device 100 and/or the separate component 110 can be reusable. In particular, the separate compartment 110 can be reprogrammed. For example, the sampling device 100 can be reconfigured e.g. to a different sampling rate. That is, sampling device 100 can be user defined, rather than fixed. The device 100 allows some flexibility in its configuration. This is achieved through the serial communications chip and associated software.

In some embodiments, the separate compartment 110 includes any associated electronics 128 circuits and at least a battery. Preferably, the separate compartment 110 includes at least a battery 120, a sensor 128B and a microprocessor 128E.

Figure 10:
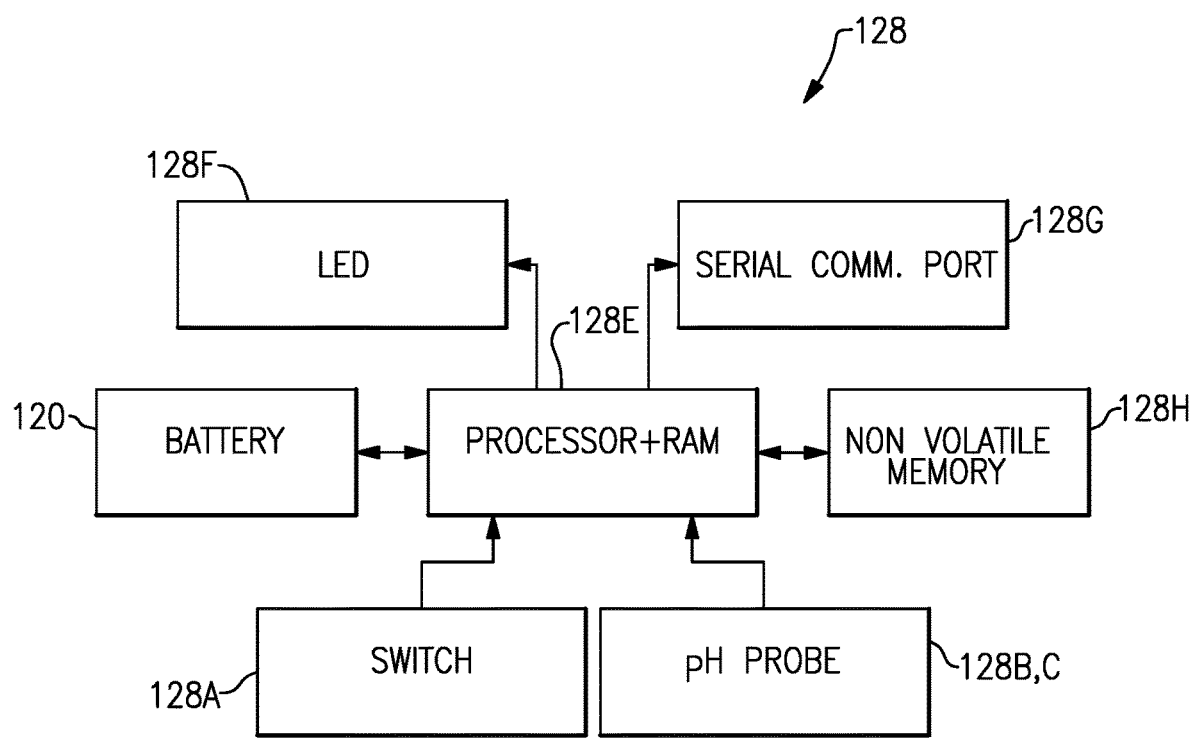
FIG. 10 is a schematic diagram of the different electrical components that can be included in some embodiments of the separate component.

Typically, the device 100 may comprise a printed circuit board 128E that includes a microcontroller (PIC microcontroller), a sensor (such as a glass pH microelectrode 128B and a pH reference microelectrode 128C), a light emitting diode 128E, a release detect switch 128A, a battery connection (not shown), various resistors and capacitors and/or a power source. FIG. 10 is a schematic diagram showing the different electrical components that can be in the separate compartment 110 of the sampling device 100.

The sampling device 100 may include a battery 120. In particular, such a battery 120 is within the separate compartment 110.

The battery 120 can be any form of battery known in the art, such as a pin of carbon monofluoride lithium or a coin cell. Coin cell batteries can be made of alkaline, lithium, silver, etc. and or combinations thereof and are available in different sizes.

In particular, the battery is capable 120 of running for at least 24 hours. The battery may be rechargeable.

The separate compartment 110 may comprise one or more batteries 120.

Figure 11:
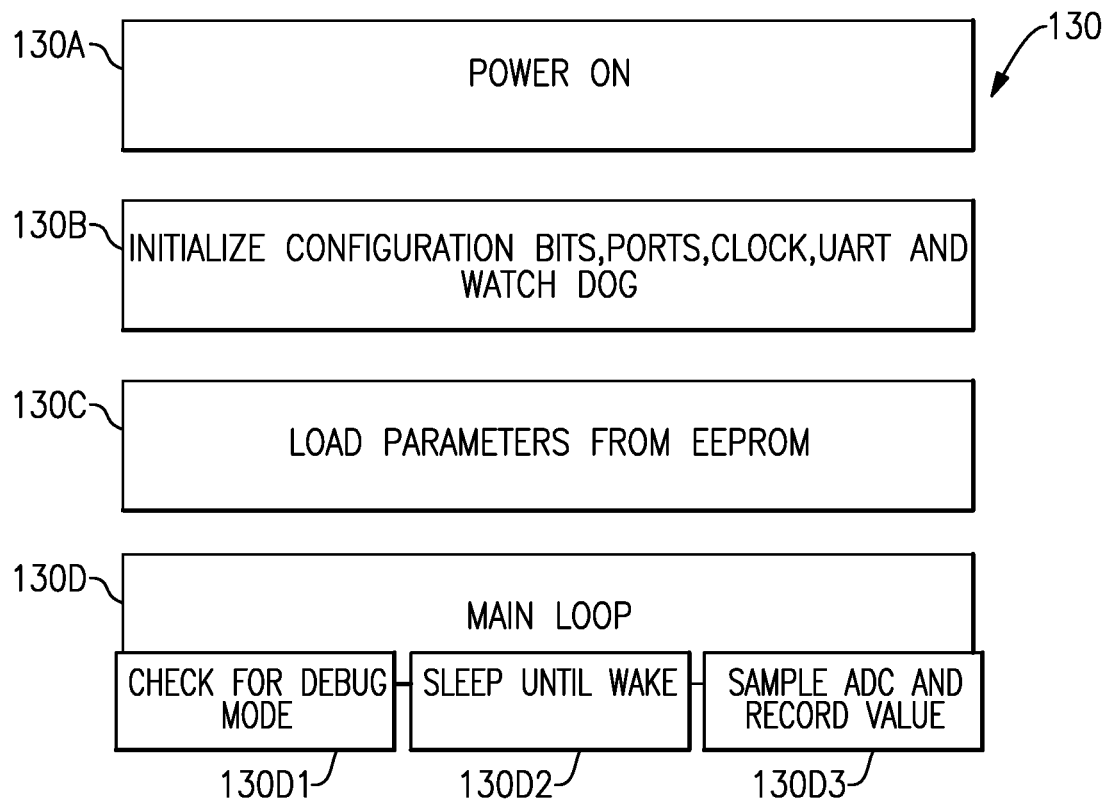
FIG. 11 is a schematic diagram of one example of a main loop cycle that may be carried out by the electronic circuitry of one embodiment of a sampling device.

Essentially the device 100 can be turned on when the battery is inserted; the device 100 initializes and then repeatedly goes through a main loop cycle comprising the steps of powering on 130A→initializing configuration bits, ports, clock, UART, and Watchdog 130B→Load parameters from EEPROM 130C→Main Loop 130D comprising checking for debug mode 130D1, sleep until wake 130D2 and sample ADC and record value 130D3. This main loop cycle is also shown in FIG. 11.

Typically, on being powered on 130A the software initializes and defines configuration bits, ports, clock, universal asynchronous receiver/transmitter and watchdog timer 130B.

Parameters are loaded from the electronically erasable programmable read-only memory 130C, wherein the parameters to be loaded can be a device ID, a log address, sample rate, pre-wake time, burst count and sample number.

The device ID is the serial number of the device 100. The log address is the address at which the next logged data will be stored. The sample rate is the sample rate of the data logging. The pre-wake time is set to allow the microprocessor 128E to reach normal operating condition. The burst count is the number of samples taken per interval and sample number is the number of samples taken before the sample is obtained and recorded.

The device 100 then enters a main loop 130D, wherein it checks for the presence of a serial interface 128E. If the serial interface 128E is present, the device 100 enters a debug mode 130D1 in which various parameters can be manipulated. In the absence of a serial interface, the watchdog timer instigates a wake event during which data is sampled from the analogue digital converter and recorded 130D3 to flash memory 128H. The device 100 can then re-enter sleep mode 130D2 until the watchdog timer instigates a further wake event.

In some embodiments, the separate compartment 110 further comprises flash memory 128H, which is capable of recording data. The data is stored and then downloaded when the separate compartment 110 is recovered or is transmitted live to a remote facility (i.e. via wireless data transmission).

The wireless data transmission system may consist of two parts. The first part is the device 100, which contains radio frequency transmitter circuitry, antenna and processing means with firmware to control transmissions, for example a microchip inserted in the device 100 (such as radio frequency identification (RFID)). The second part consists of radio frequency receiver circuitry and an antenna. Such wireless transmission is also effective in locating the device 100.

The second part has a range of possible embodiments, including but not limited to a mat which can be placed on the floor of a kennel; a small unit which can be floor, wall or ceiling mounted; a collar, belt, jacket, boot, ear piercing or another form which can be carried externally by the animal or placed in the external environment of the closed system in which the device 100 is being used (such as outside a fish tank, outside factory pipes, etc.).

The second part also includes a means of storing received data and communicating that data to operators or other equipment. Communication to the user either via the first part or second part of the wireless data transmission may be in the form of illuminated indicators, speakers or sounders, or a graphical display, for example available signals (such as buzzers).

Communicated data between the first part and the second part may include but is not limited to measurements of pH by the device 100; measurements of temperature by the device 100; measurements from other sensors by the device 100, other status information from the device 100, such as battery level, sample capture status etc.; data that has been intelligently processed by the device 100 and is derived from other readings, for example alerts to indicate the estimated position of the device 100 within the gastrointestinal tract (i.e. leaving the stomach; entering ileum, etc.).

Communication by the second part to other equipment may include standard or proprietary wired communications interfaces (e.g. Ethernet, USB, serial cable etc.), standard or proprietary wireless communications (e.g. Bluetooth, GSM, wifi), removable data storage such as SD card, USB data 'key' etc.

The separate compartment may comprise a switch 128A. In particular, the switch 128A is adapted to record the time at which the separate compartment 110 is ejected from the housing 102 of the sampling device 100.

The switch 128A can be a contact switch or a non-contact switch. The contact switch may be a reed switch, pressure switch or a non-contact switch which can be an inductive coil, built within the microprocessor or an optical switch, such as an LED and photodiode pair.

Preferably, the switch 128A can be a pressure switch.

The pressure switch 128A interfaces with a small protrusion 108D on the upper surface of the actuation means 108 (e.g. the plunger/piston 108B). The actuation means 108 and the separate compartment 110 apply pressure to one another and thereby maintain contact with one another by means of the protrusion 108D and pressure switch 128A. In particular, when the retention means 112 releases or is otherwise activated, the separate compartment 110 is at least partially released and at least partly disengaged from the actuating means 108.

In particular, the switch 128A is closed when the separate compartment 110 and the actuation means 108 are engaged. When the separate compartment 110 and the actuation means 108 are disengaged the switch 128A is open. Typically, when the switch 128A is open, it is after the time at which the sample has been obtained and the separate compartment 110 has been ejected from the device 100.

In alternative embodiments, the switch 128A can be a reed switch. The reed switch can be kept in the closed configuration by a magnet located on the actuation means 108 in particular within the protrusion 108D on the actuation means 108. When the separate compartment 110 is ejected, the magnet and reed switch are no longer in contact, the reed switch is therefore open and provides a signal that a sample has been captured.

In other embodiments, the switch 128A can be an inductive coil. The inductive coil arrangement exists between the actuation means 108 and the separate compartment 110, whereby a current is induced in the coil of the separate compartment 110. When the separate compartment 110 is ejected, the induced current in the coil of the separate compartment 110 is no longer present, signalling that the sample has been captured.

In yet other embodiments, the switch 128A can be an optical switch. The optical switch can be a small light source (e.g. a light emitting diode) and a light dependent resistor that are arranged between the actuation means 108 and the separate compartment 110, such that the light affects the electrical resistance of the light dependent resistor. When the separate compartment 110 is ejected, the light source is no longer able to affect the light dependent resistor and the resulting change in resistance is interpreted as a signal that the sample has been captured.

The sampling device 100 may include a sensor 128B, C. In particular, the separate compartment includes the sensor 128B, C. In particular, the sensor may be a pH sensor 128B, C and/or a temperature sensor. Other sensors that are capable of sensing and signaling other environmental factors, such as pressure, solute etc. can also be used in the device 100.

In particular, the sensor 128B, C may protrude from the surface of separate compartment 110 so that it is exposed to the external environment of the sampling device 100.

In preferred embodiments, the sensor 128B, C is a pH sensor/meter, which can include a glass pH microelectrode 128B and a pH reference microelectrode 128C.

A typical pH meter consists of a measuring probe (such as a glass electrode) 128B and a reference probe 128C connected to an electronic meter that measures and displays or logs the pH reading. A variety of pH meters are known in the art that can be used in this invention. The preferred pH sensing components in the present invention consist of a glass microelectrode 128B coupled with a reference microelectrode 128C. Alternative embodiments may consist of ion selective field effect transistors, solid state reference electrodes, or other suitable technology readily known in the art.

In particular, the printed circuit board of the device 100 may comprise a pH circuit. The circuit can log the pH level during the transit of the device 100 (e.g. along the gastrointestinal tract), wherein the circuit comprises at least a pH electrode 128B, a reference electrode 128C, a microprocessor 128D, a switch assembly and a power source 120.

Typically, the software and electronics will interface with a miniaturized pH probe input to an analogue digital converter, a reference voltage to the pH reference electrode, a switch contact that detects the device configuration status as either open or closed, a universal asynchronous receiver/transmitter (UART) to download saved data and perform diagnostic functions, a UART connected detect circuit, and an LED connected to the UART transmit.

In some embodiments, the pH probe circuit is designed without amplifiers, but instead limits the positive and negative references for the analogue digital converter in the microcontroller to the appropriate the range of output voltage. The reference voltage of the sensor is offset with a simple resistor divider network. A processor is required which includes a voltage reference which can be output, and an analogue digital converter. In using fewer components compared with a more conventional design, the pH probe more easily fits into a small space. A reduced circuit with a simple resistor divider network in place of amplifiers represents a suitable approach for the requirements of the sampling device 100.

Typically, a pH sensor 128B is dependent on the pH condition in which it is embedded, which can be preprogrammed to react/respond to a certain pH condition depending on the external environment in which the device 100 is placed, for example the location along the gastrointestinal tract and/or a tank (i.e. for bioprocessing/fish/other processing etc.) and/or other agricultural systems. The pH sensor can be preprogrammed to activate at pH levels of 1, 2, 3, 4, 5, 6, 7, 8, 9, 10, 11, 12, 13 or 14 and/or any ranges and/or combinations thereof. For example, a pH below 4 can be preprogrammed so that the device 100 is activated to its second configuration (e.g. in the stomach), or preprogrammed at pH above 5 so that the device 100 is activated to its second configuration (e.g. in the small or large intestines and/or just upon entry to the small or large intestine). The activation may include a temporal element such that activation is delayed for a predetermined time following detection of a specific pH level. The activation may also be programmed such that a consistency of pH level is required before activation is triggered. For example, so that the retention means 112 is not released.

In particular, the glass electrode may protrude from the surface of the separate compartment 110, so that it is exposed to the external environment of the sampling device 100 to be capable of measuring the pH at an accuracy of +/−0.5 pH units (5% accuracy) and able to take multiple readings (for example about 3000 readings or more), which can be preconfigured to determine the rate the pH is measured and logged.

In particular, the sensor/meter 128B may be connected to the battery 120 and the associated electronic circuits 128 within the separate compartment 110.

Further, the circuit can also log the actuation moment at which point the sample is drawn into the housing 102 (i.e. collected). This is achieved by monitoring the release of the switch 128A (i.e. when the switch 128A is open and no longer in contact and/or engaged with the actuation means 108).

In some embodiments, the device 100 may further include a temperature sensor, a pressure sensor, an ultra sound sensor, a biosensor and/or a solute sensor, or the like.

In some embodiments, the sensor/meter 128B can be programmed to release the retention means 112 relative to a particular pH unit, timing, temperature solute concentration or any combinations of these parameters. For example, such programming may include: a timing of 60 minutes after the pH increases to about pH3 or 60 minutes after pH has risen for at least 2 pH units and remained elevated for 3 consecutive minutes, etc.

In some embodiments, the sampling device 100 further comprises a retention means 112 which releasably retains the separate compartment 110 within the housing 102 of the sampling device 100. In particular, the housing 102 of the sampling device 100 includes a retention means 112.

The retention means 112 temporarily prevents the actuation means 108 (e.g. plunger/piston 108B) from ejecting from the housing 102 until a predetermined time and/or condition. The retention means 112 can be any element or object or mechanism which prevents the separate compartment 110 from being released from the housing 102 of the device 100. In particular, the retention means 112 holds the separate compartment 110 within the housing 102 of the device 100 and maintains the actuation means 108 in a compressed state and thus, the device 100 in a closed configuration.

The retention means 112 can be can be passively or actively activated.

In particular, the retention means 112 can be activated automatically, preprogrammed and/or activated remotely. Various embodiments of the retention means are shown in FIGS. 8A-8L.

Figure 8B:
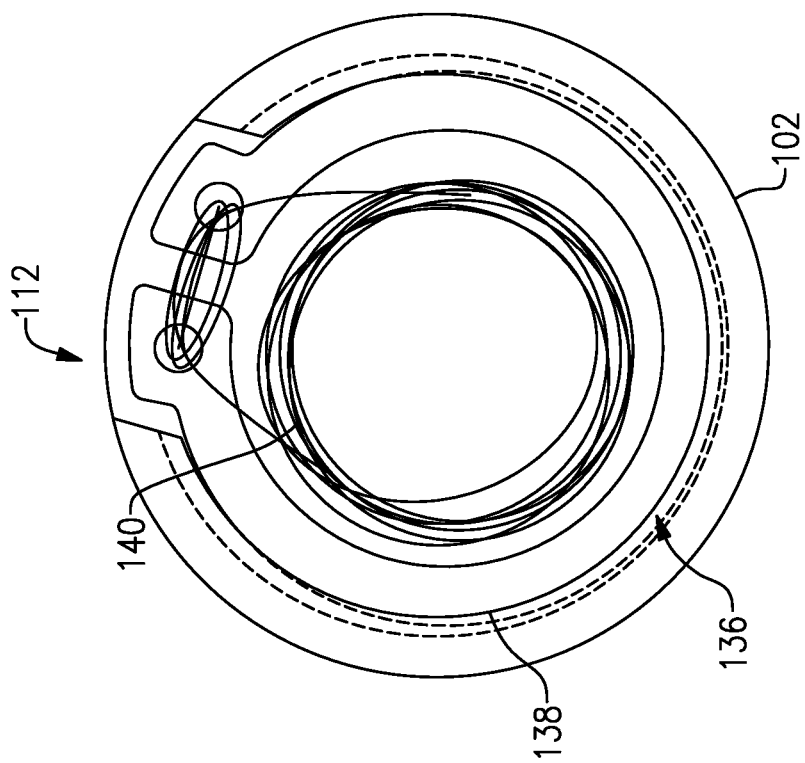
FIGS. 8A to 8L are schematic illustrations of additional embodiments of retention means.
Figure 8A:
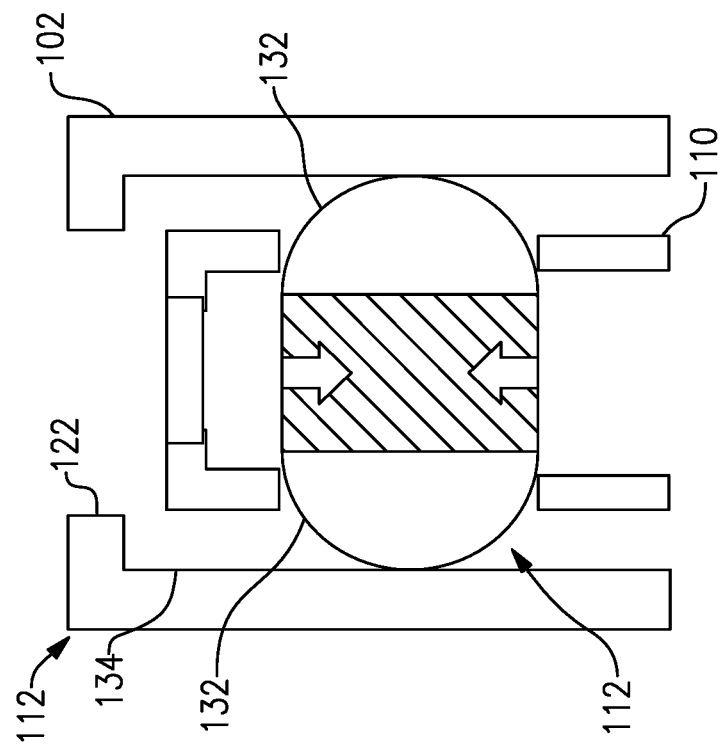

FIG. 8A shows an embodiment of retention means 112 comprising a radial interlocking mechanism which is a bowed member friction. Bowed elements 132 protruding from the sides of the separate compartment 110 interfere with the inner surface 134 of the housing 102 to cause friction. This friction prevents the separate compartment 110 from being released. The elements 132 are kept in a bowed configuration by a force generated by a trigger means (not shown), for example current being passed through a piezoelectric stack. When the electric current is switched off, the bowed elements 132 relax, reducing the friction and allowing the separate compartment 110 to be released from housing 102.

FIG. 8B shows an embodiment of retention means 112 comprising a radial interlocking mechanism which is a circlip 136. A circlip 136 is fitted into a groove (not shown) on the outer circumference of the separate compartment (not shown in FIG. 8B). The circlip 136 interferes with a second groove 138 on the inner face of the housing 102, preventing the separate compartment from being released. The trigger means may be a length of muscle wire 140 that shortens when a current is passed through, squeezing together the circlip 136 such that its circumference is reduced, allowing the separate compartment 110 to be released.

Figure 8D:
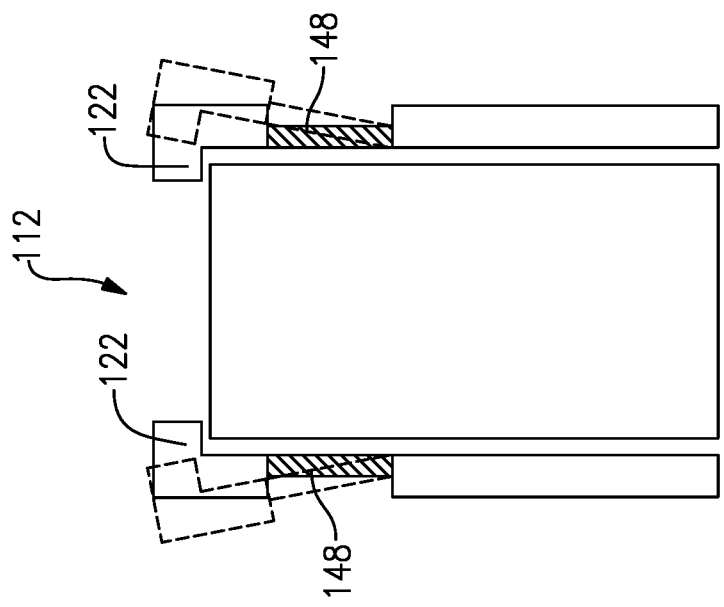
Figure 8C:
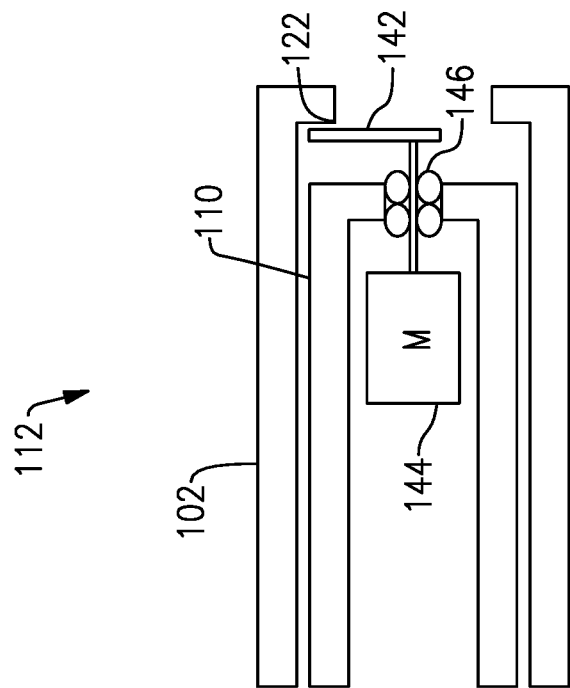

FIG. 8C shows an embodiment of retention means 112 comprising a rotary interlocking mechanism which is a rotating catch (such as a rotating point catch). A rotatable arm 142 protrudes from the separate compartment 110 to interfere with a lip 122 on the end of the housing 102, preventing the separate compartment 110 from being released. A trigger means, for example an electronic motor 144, causes the arm 142 to rotate on a sealed bearing 146, such that the arm 142 no longer interferes with the lip 122, allowing the separate compartment 110 to be released.

FIG. 8D shows an embodiment of retention means 112 comprising a linear interlocking mechanism which is a deformable barrel. The separate compartment 110 is prevented from being ejected by protrusions 122 on the end of the housing 102. Opposite sections 148 of the housing 102 are made from a deformable material, such as a piezoelectric material. When a current is passed through the piezoelectric material, it deflects outwards away from the separate compartment 110. The protrusions 122 no longer cause an obstruction and the separate compartment 110 is released.

Figure 8F:
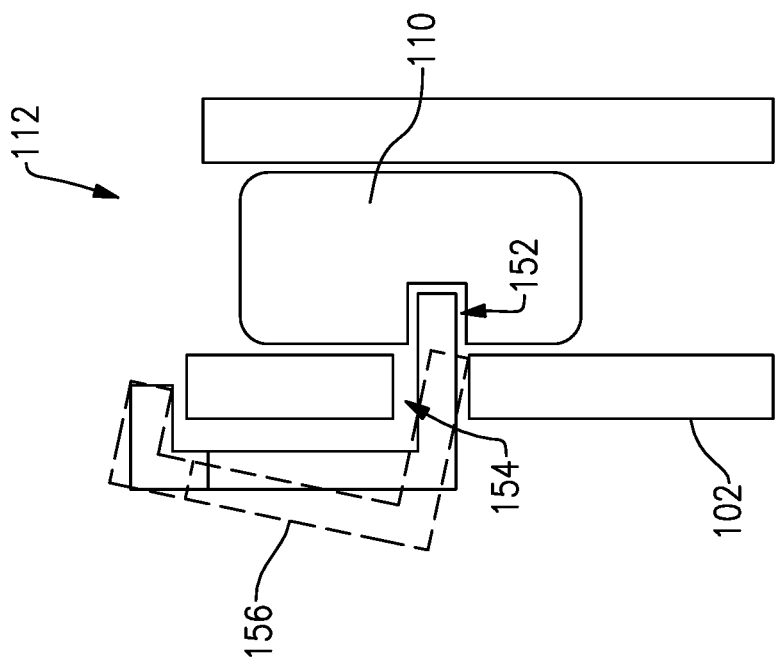
Figure 8E:
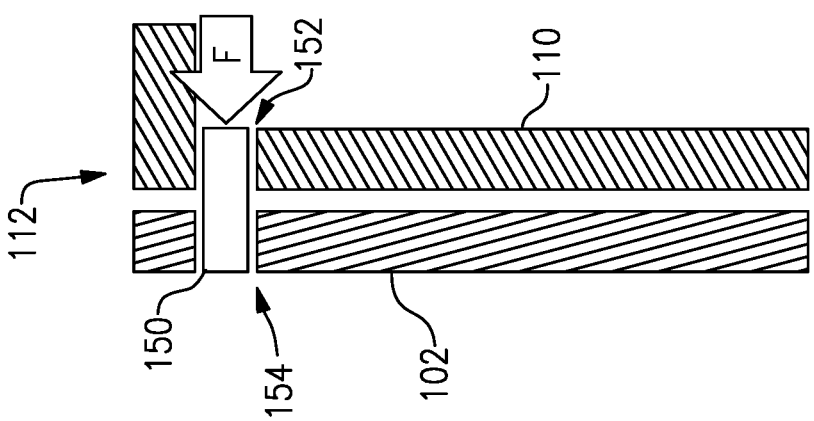

FIG. 8E shows an embodiment of retention means 112 comprising a linear interlocking mechanism which is a pin 150. A pin 150 protrudes though an opening 152 in the separate compartment 110 into a recess hole 154 in the housing 102, preventing the separate compartment from being released. A trigger means, for example a solenoid device (not shown), provides a force F which pushes the pin 150 outwards through the hole 154 in the housing 102, allowing the separate compartment 110 to be released.

FIG. 8F shows an embodiment of retention means 112 comprising a linear interlocking mechanism which is a bi-metallic latch. A bi-metallic latch 156 protrudes though an opening 154 in the housing 102 and interferes with a recess 152 in the separate compartment 110 preventing the separate compartment 110 from being released. A trigger means, for example an electronic heating coil (not shown), heats the bi-metallic latch/or pin 156 such that it is deflected or deformed. This change caused the bi-metallic latch (or pin) 156 to disengage from the recess or hole 152 in the separate compartment 110, allowing it to be released. (Q=heat)

Figure 8H:
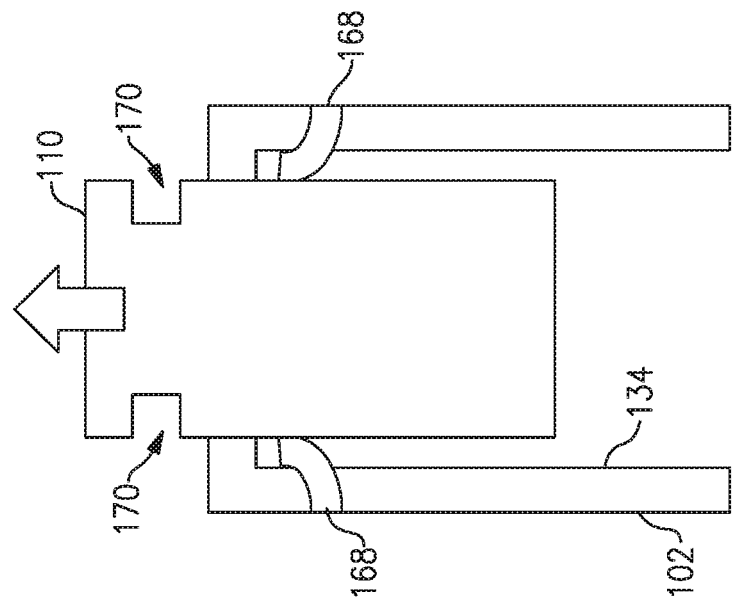
Figure 8G:
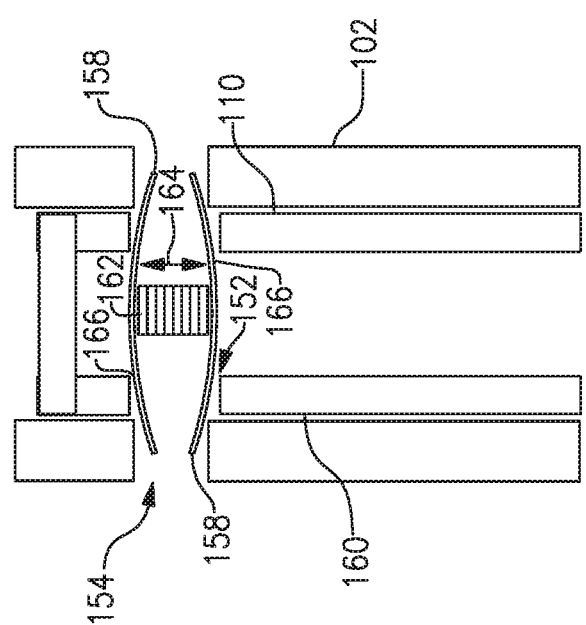

FIG. 8G shows an embodiment of retention means 112 comprising a radial interlocking mechanism which is a pull-in catch. Two deformable members 166 protrude from the surface 160 of the separate compartment 110 into holes 154 in the housing 102, preventing the separate compartment 110 from being ejected. A trigger means, for example a piezoelectric stack 162, causes the deformable members 166 to be pushed in a direction 164 parallel to the length of the device 100. This causes the ends 158 of the deformable members 166 to be retracted inwards away from the housing 102, allowing the separate compartment 110 to be released.

FIG. 8H shows an embodiment of retention means 112 comprising a linear interlocking mechanism which is a deformable pin. Two elements 168 protrude from the surface 134 of the housing 102 into recesses 170 in the separate compartment 110, preventing the separate compartment 110 from being released. The elements 168 are deformable, for example being made from a shape memory alloy. When a current is passed through the elements 168, their consistency changes such that the elements become softer and the force of the actuation means is able to deform elements 168 to an extent that the separate compartment 110 is released.

Figure 8J:
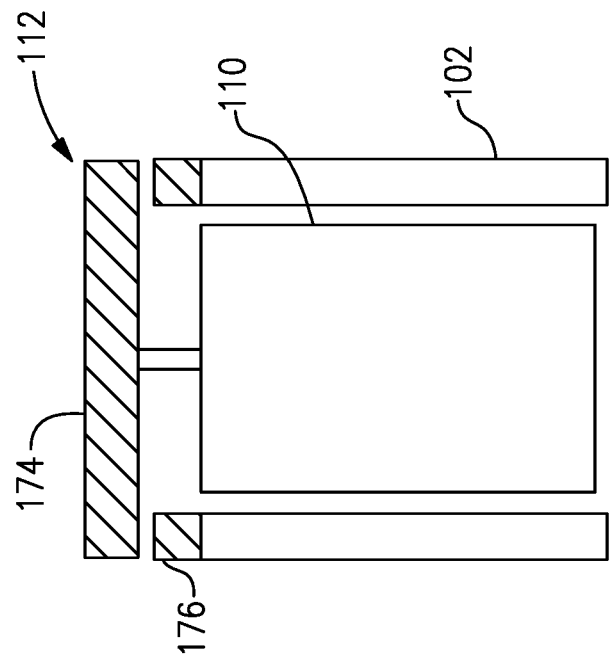
Figure 8I:
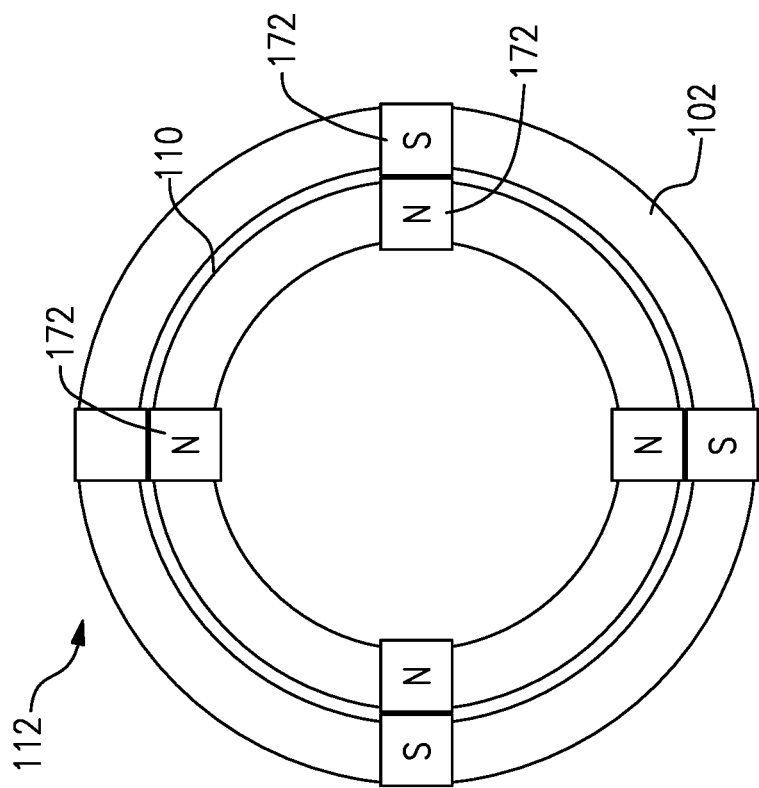

FIG. 8I shows an embodiment of retention means 112 comprising a rotary interlocking mechanism which comprises magnets. Magnets 172 are embedded in the surface of the separate compartment 110 and the housing 102 are aligned such that there is an attractive force between them. This attractive force prevents the separate compartment 110 from being released. A trigger means, for example an electric motor (not shown), causes the magnets 172 to become misaligned, or aligned in such a way that the magnetic poles repel. This removes the attractive force between the magnets 172, allowing the separate compartment 110 to be released.

FIG. 8J shows an embodiment of retention means 112 comprising is a linear interlocking mechanism which are electromagnets (electromagnetic). An end surface 174 of the separate compartment 110 consists of a ferrous material. The end 176 of the housing 102 is made from a ferrous electromagnet. A current is passed through the electromagnet, generating an attractive force between the end 176 of the housing 102 and the end surface 174 of the separate compartment 102, preventing the separate compartment 110 from being released. When the current is removed, the attractive force no longer exists and the separate compartment 102 can be released.

Figure 8K:
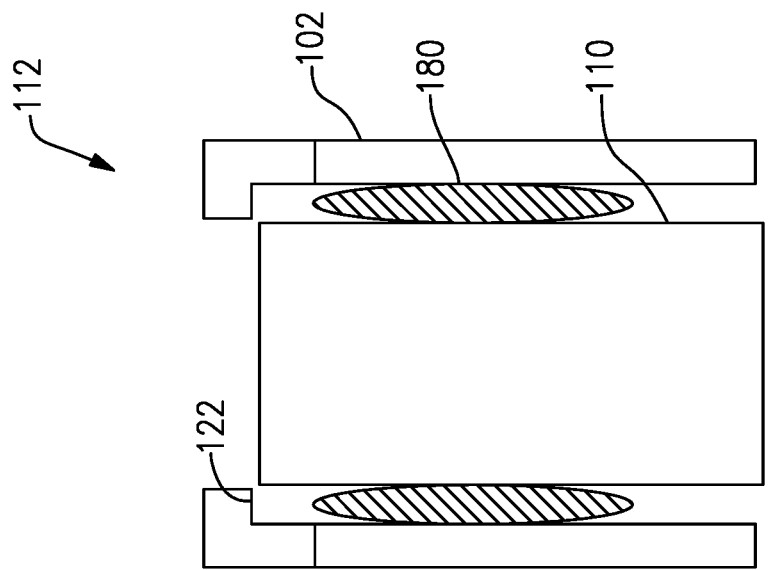

FIG. 8K shows an embodiment of retention means 112 comprising a thermal sensitive material 178. The separate compartment 110 is prevented from being released by a material 178 that degrades when heated, such as a wax. Upon heating, the material 178 becomes soft and is no longer able to resist the force of the actuation means 108 and the separate compartment 110 is released.

Figure 8L:
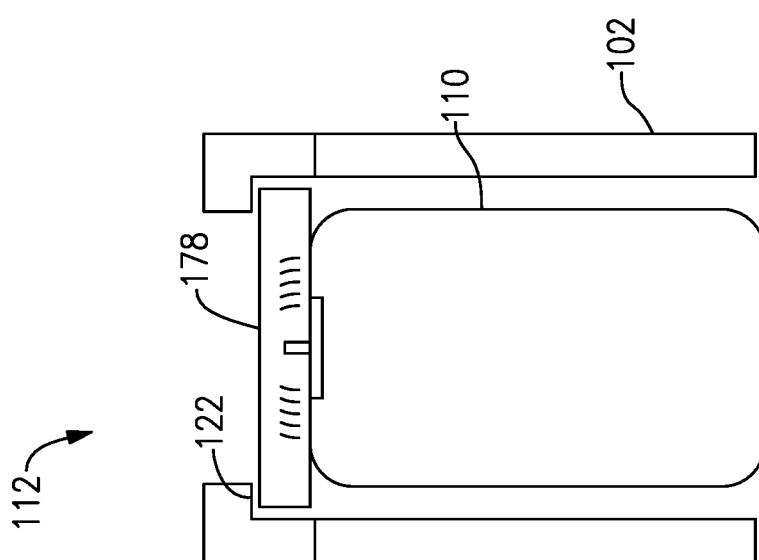

FIG. 8L shows an embodiment of retention means 112 comprising a photo sensitive material 180. The separate compartment 110 is prevented from being released by friction caused by a glue or glue-like material 180 between the separate compartment 110 and the housing 102. When the material 180 is exposed to light, for example being exposed to a light emitting diode, the (glue) material 180 degrades and the separate compartment 110 is released.

In some embodiments, the retention means 112 can be a material that reacts to changes in the external environment of the device 100 and/or an interlocking mechanism and/or a fastening means.

In some embodiments, the retention means 112 can be a material that reacts to changes in the external environment of the device 100. The retention means 112 can be in the form of a coating, pin and/or washer. In preferred embodiments, the retention means 112 is in the form of a coating. The coating may surround the entire device 100 or may partially cover only certain parts of the device 100 or be located at a particular part of the device 100.

Typically, the device 100 can encounter differences in physiological characteristics, such as pH, pressure, temperature, enzymatic activity, etc. (e.g. depending on whether the device is in the stomach, the colon, etc., especially when travelling along the gastrointestinal tract of an animal). The external environment of the device 100 is therefore variable. In particular embodiments, the sampling device 100 can comprise a retention means 112 that is a material that reacts to pH, temperature, light, moisture, solute concentration or enzyme activity or concentration. In particular, the material can be degradable, digestible or soluble.

The material may surround the entire device 100 or may partially cover only certain parts of the device 100 or be located at a particular part of the device 100. The material may be located and/or cover the end of the device 100 which ejects the separate compartment 110. The material may also cover the opening 106, for example the inlet, outlet 106B and/or inlet 106 and outlet 106B. In particular, the material may be in the form of a coating, pin and/or washer.

In some embodiments, the retention means 112 can be a material that reacts to changes in the external environment, wherein the retention means 112 is a material in the form of a coating. The coating may surround the entire device 100 and/or parts of the device 100. The coating aids the device 100 to retain the separate compartment 110 within the housing 102.

In some embodiments, the retention means 112 can be a material that reacts to changes in the external environment, wherein the retention means 112 is a material in the form of a washer. The washer aids to retain the separate compartment 110 with the housing 102.

In some embodiments, the retention means 112 can be a material that reacts to changes in the external environment, wherein the retention means 112 is a material that can be in the form of a coating and a washer, thereby retaining the separate compartment 110 within the housing 102 and also maintaining the washer dry and keeping the mechanical strength of the washer intact.

In such embodiments, the material of the retention means 112 dissolves gradually upon contact with a change in pH, a change in temperature, a change in light, a change in moisture, a change in solute concentration or enzymatic environment. The rate of degradation, digestibility and or solubility may be controlled by either differences in the chemical structure of the material or by differences in the thickness of the application and/or form of similar materials, or both. In particular, the material may require two or more layers of the same material or of different materials.

In some embodiments, the pH-sensitive material may comprise and/or consist of a pH-sensitive material that degrades in an alkaline environment or in an acidic environment. The rate of degradation may be controlled by either differences in the chemical structure of the material or by differences in the thickness application and/or form of similar materials, or both.

In some embodiments, a first material/layer of the retention means 112 is dissolved in response to a first pH, first temperature, first wavelength of light, first soluble concentration or first enzymatic activity, and a second material/layer is dissolved in response to a second, different pH, different temperature, different wavelength of light, different solute concentration or different enzymatic activity.

The material can be pH dependent and dissolve in the stomach when in contact with gastric acid and in acidic conditions under pH 4 or in the large intestine when in alkaline conditions such as a pH 5 to 6 or above 7, and/or any combinations thereof.

In particular embodiments, the material can be cellulose, acetate phthalate, glycerol stearates, paraffin, epoxy compounds or poly (methyl) acrylates, such as Eudragit® L, S or E. Preferably, the material is Eudragit® L, S or E.

In some embodiments, the material may comprise and/or consist of a temperature sensitive material that degrades upon an increase or decrease in temperature. The heat-sensitive material may be glue, glue-like material or wax. In particular, the wax may be paraffin wax, microcrystalline wax, ester wax, polyester wax or vegetable wax. The preferred embodiment can be paraffin wax with a melting point above the body temperature of the animal. FIGS. 8F and 8K show embodiments wherein retention means 112 comprises a thermally sensitive material.

In some embodiments, the retention means 112 may comprise and/or consist of a photo-sensitive material 180 that degrades upon a certain wavelength, such as glue and/or other like materials known in the art. In particular, when the material 180 is exposed to light, for example being exposed to a light emitting diode, the (glue) material 180 degrades. FIG. 8L represents an example of a photo-sensitive material as a retention means.

In some embodiments, the material may comprise and/or consist of material that degrades upon a change in moisture of solute concentration.

In some embodiments, the material may comprise and/or consist of material that degrades upon a change in enzyme activity and/or concentration.

In alternative embodiments, the retention means 112 can be an interlocking mechanism. In particular, the interlocking mechanism can be between the housing 102 and the separate compartment 110. In some embodiments, the retention means 112 may comprise a material that reacts to changes in the external environment of the device 100 and an interlocking mechanism. The material that reacts to changes in the external environment may react to pH, temperature, light, moisture, solute concentration or enzyme activity or concentration. In particular, the material can be degradable, digestible or soluble.

The material may surround the entire device 100 or may partially cover only certain parts of the device 100 or be located at a particular part of the device 100. The material may be located and/or cover the end of the device 100 which ejects the separate compartment 110. The material may also cover the opening 106, for example the inlet, outlet and/or inlet and outlet 106B. In particular, the material may be in the form of a coating, pin and/or washer. The material may be in the form of a coating.

The material dissolves gradually upon contact with a change in pH, a change in temperature, a change in light, a change in moisture, a change in solute concentration or enzymatic environment. The rate of degradation, digestibility and or solubility may be controlled by either differences in the chemical structure of the material or by differences in the thickness of the application and/or form of similar materials, or both. In particular, the material may require two or more layers of the same material or of different materials.

In some embodiments, the pH-sensitive material may comprise and/or consist of a pH-sensitive material that degrades in an alkaline environment or in an acidic environment. The rate of degradation may be controlled by either differences in the chemical structure of the material or by differences in the thickness application and/or form of similar materials, or both.

In some embodiments, a first material/layer is dissolved in response to a first pH, first temperature, first wavelength of light, first soluble concentration or first enzymatic activity, and a second material/layer is dissolved in response to a second, different pH, different temperature, different wavelength of light, different solute concentration or different enzymatic activity.

The material can be pH dependent and dissolve in the stomach when in contact with gastric acid and in acidic conditions under pH 4 or in the large intestine when in alkaline conditions such as a pH 5 to 6 or above 7, and/or any combinations thereof.

In particular embodiments, the material can be cellulose, acetate phthalate, glycerol stearates, paraffin, epoxy compounds or poly (methyl) acrylates, such as Eudragit® L, S or E. Preferably, the material is Eudragit® L, S or E.

In some embodiments, the material may comprise and/or consist of a temperature sensitive material that degrades upon an increase or decrease in temperature. The heat-sensitive material may be glue, glue-like material or wax. In particular, the wax may be paraffin wax, microcrystalline wax, ester wax, polyester wax or vegetable wax. The preferred embodiment can be paraffin wax with a melting point above the body temperature of the animal. FIGS. 8F and 8K show embodiments wherein retention means 112 comprises a thermally sensitive material.

In some embodiments, the material may comprise and/or consist of a photo-sensitive material that degrades upon a certain wavelength, such as glue and/or other like materials known in the art. In particular, when the material is exposed to light, for example being exposed to a light emitting diode, the (glue) material degrades. FIG. 8L shows an embodiment wherein retention means 112 comprises a photo-sensitive material.

In some embodiments, the material may comprise and/or consist of material that degrades upon a change in moisture of solute concentration.

In some embodiments, the material may comprise and/or consist of material that degrades upon a change in enzyme activity and/or concentration.

Typically, an interlocking mechanism is a mechanical element allowing coupling of one or more elements which is/are capable of affecting the separate elements and/or other objects in motion or operation.

In particular, the interlocking mechanism can be fastened or released by rotary, radial or linear motion or means.

In particular, the retention means 112 can be a (i) rotational (i.e. rotary) interlocking mechanism or (ii) a radial interlocking mechanism or (iii) a linear interlocking mechanism.

In some embodiments, the interlocking mechanism may be rotary, such as a bayonet mount, a rotating point catch, a set of rotating magnets or electromagnets (see representations of these in FIGS. 8C and -8I). Preferably, the rotary interlocking mechanism is a bayonet mount.

Bayonet mounts are typically known in the art as fastening elements which consist of a male side with one or more radial pins, and a female receptor with matching L-shaped slot(s) and with spring(s) to keep the two parts engaged and locked together. The slots may be shaped like a capital letter L with serif (a short upward segment at the end of the horizontal arm); the pin slides into the vertical arm of the L, rotates across the horizontal arm, then is pushed slightly upwards into the short vertical "serif" by the spring; the connector is no longer free to rotate unless pushed down against the spring until the pin is out of the "serif" and therefore unlocked and released.

Figure 5A:
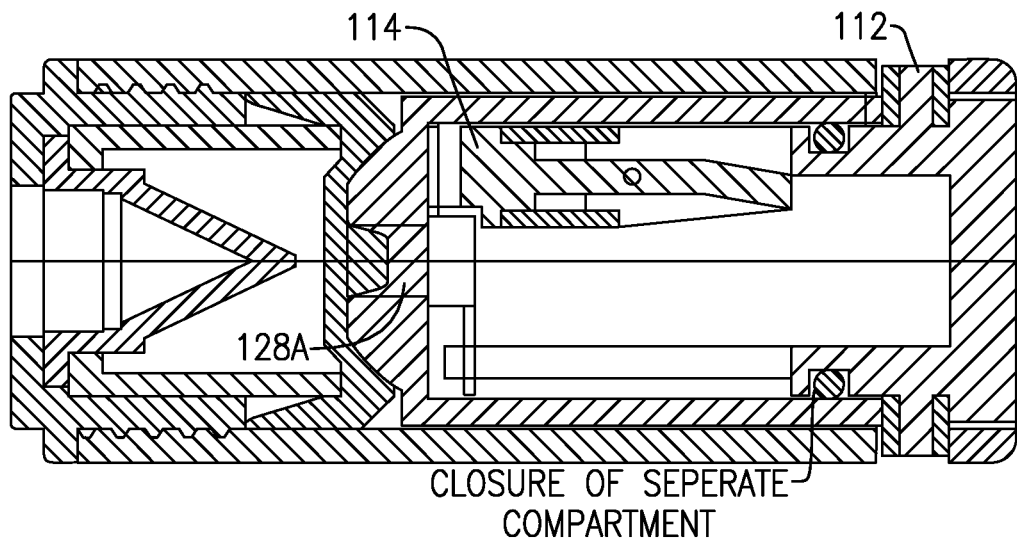
FIG. 5A is a cross-sectional view of one embodiment of a retention means in a primed and released state.
Figure 5B:
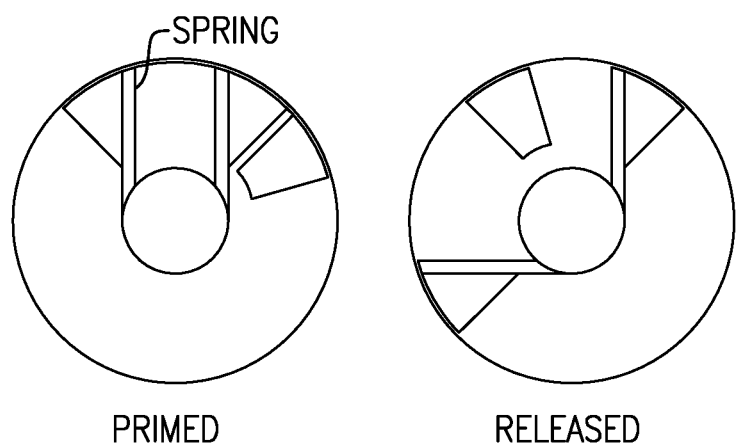
FIG. 5B is a cross-sectional view of one embodiment of the sampling device, incorporating the retention means shown in FIG. 5A.

In particular, wherein the retention means 112 can be a bayonet mount, the actuation means 108 (e.g. the plunger/piston 108B) is attached into the device opening 106 such that it cannot rotate when in the compressed condition. The separate compartment 110 is made to pivot against this attachment until the bayonet mount interlocking mechanism is aligned in such a way that the separate compartment 110 is no longer retained and thus the separate compartment 110 is released. Thereby, releasing the pressure in the housing 102 of the device 100 and thus the actuation means 108 is expanded along the housing 102 pushing the separate compartment 110 out of the device 100 from the first compressed configuration to the second expanded configuration. One embodiment of the retention means 112 comprising a bayonet mount is shown in FIGS. 5A and 5B.

In particular embodiments, the rotary mechanism can be a rotating point catch. In particular, a pin 142 can interfere with the stopper means 122 on the housing 102 of the device 100. On activation, the pin 142 is rotated by a driving force such that it clears the stopper means 122 and the separate compartment 110 is released. FIG. 8C shows one embodiment wherein retention means 112 comprises a rotating point catch interlocking mechanism.

In particular embodiments, the rotary mechanism can be a set of rotating magnets. In particular, permanent magnets 172 are included in the wall of the housing 102 and separate compartment 110. When held in alignment, the attraction of the magnets 172 holds the separate compartment 110 within the housing 102 of the device 100. When exposed to a rotating force, the magnets 172 are moved out of alignment and the force of attraction is lost. The separate compartment 110 is then released. FIG. 8I shows one embodiment wherein retention means 112 comprises rotating magnets 172 as a rotary interlocking mechanism.

In particular embodiments, the rotary mechanism can be electromagnetic. In particular, electromagnets embedded into the walls of the separate compartment 110 and the housing 102 are energized such that they are attracted. This attraction is sufficient to prevent the separate compartment 110 from moving against the housing 102. On removal of the energising current, the two compartments are no longer held by an attractive force and the separate compartment 110 is then released.

In some embodiments, the interlocking mechanism can be radial, such as a compressible material (i.e., an O-ring as shown in FIG. 1-4, 6), bowed member friction, a circlip or a pull in catch (see representations of these in FIG. 8A, 8B or 8G). Preferably, the radial interlocking mechanism is a compressible material such as rubber O-ring washer.

In particular embodiments, the radial interlocking mechanism can be any compressible material. In some embodiments, the material may be elastomeric. In particular, the compressible material may be an O-ring washer (112 in FIGS. 1-4 and 6) or a bending strip element. In particular, the ring of compressible material is compressed between the lid 110B and body 110A of the separate compartment 110. This compression causes the material of the O-ring to expand outwards (radially) such that it comes into contact with the inner face of the housing 102 of the device 100. The resulting friction is sufficient to prevent the separate compartment 110 from being ejected. The compression of the ring 112 is reduced at a particular condition and/or predetermined time, reducing the friction between the separate compartment 110 and the housing 102 and thereby releasing the separate compartment 110. In this fashion, the O-ring 112 releasably retains the separate compartment 110.

In particular embodiments, the radial interlocking mechanism can be a bowed member. In particular, bowed elements 132 on the external surface of the separate compartment 110 are held in compression such that they are caused to bow out. These elements 132 come into contact with the inner surface 134 of the housing 102 of the device 100, causing a frictional interference that prevents the separate compartment 110 from being released. At a particular condition and/or predetermined time, compression of the bowed elements 132 is reduced, reducing the friction between the separate compartment 110 and the housing 102, allowing the separate compartment 110 to be released. FIG. 8A shows one embodiment wherein retention means 112 comprises a bowed member radial interlocking mechanism.

In particular embodiments, the radial mechanism can be a circlip. Typically, a circlip 136 is a form of fastener which consists of a semi-flexible metal ring with open ends, which can permit rotation but prevent lateral movement. In particular, the circlip 136 is fitted to a groove on the outer surface of the separate compartment (not shown). The circlip 136 may interfere with the stopper means 122 of the housing 102 of the device 100, or, may be fitted within a groove 138 on the inner surface of the housing 102. The circlip 136 is squeezed together at a particular condition and/or predetermined time, reducing its diameter and releasing it from groove 138 and/or allowing it to move past stopper means 122, allowing the separate compartment 110 to be released. FIG. 8B represents an example of a circlip radial interlocking mechanism.

In particular embodiments, the radial interlocking mechanism can be a pull-in catch. In particular, deformable members 166 are deformed such that they protrude through apertures 152 on the side of the separate compartment 110 and engage with holes 154 on the inside wall of the housing 102 of the device 100. These deformable members 166 thus interfere with the holes 154 of housing 102 to prevent the separate compartment 110 from being released. At a particular condition and/or predetermined time, the deformable members relax and retreat from holes 154 of housing 102, allowing the separate compartment 110 to be released. FIG. 8G shows one embodiment wherein retention means 112 comprises a pull-in catch as a radial interlocking mechanism.

In some embodiments, the interlocking mechanism may be linear, such as a deformable lip and/or barrel, tab or pin at the end of the housing 102 or pin that holds the separate compartment 110 into place or a bi-metallic latch that protrudes through the housing 102 holding the separate compartment 110 into place, electromagnets and/or a shape memory alloy (see representation of these in FIG. 8D, 8E, 8F, 8H or 8J). Preferably, the linear interlocking mechanism is a pin that pushes the separate compartment 110 into place.

In particular embodiments, the linear interlocking mechanism can be a deformable lip 122. In particular, a region 148 of the housing is made deformable, such that when pushed against, the separate compartment 110 is released. Typically, cuts (e.g. lips 122) are made into the housing 102 of the device 100, such that it becomes more easily deformed. In particular, such cuts are made of deformable material 148 such as a shape memory alloy. At a particular condition and/or predetermined time, the separate compartment 110 is pushed against the cuts 122, which fold back to allow the separate compartment 110 to be released and then return to its normal state to stop the actuation means 108 from being released. Such cuts 122 can also function as the stopper means. FIG. 8D shows one embodiment wherein retention means 112 comprises a deformable pin as a linear interlocking mechanism.

In particular embodiments, the linear interlocking mechanism can be a shape memory alloy (SMA). In particular, a shaped element consisting of a shape memory alloy is deformed, such that it interferes between the separate compartment and the housing. At a particular condition and/or predetermined time, a current may be applied, or the shape memory alloy may be heated by some other means, the shape memory alloy reverts to its original shape. The original shape is specified, such that it allows the separate compartment to be released. FIG. 8H shows another embodiment wherein retention means 112 comprises a shape memory alloy as a linter interlocking mechanism, wherein the application of a particular condition causes the protruding elements 168 comprised of a shape memory alloy to deform and allows release of the separate compartment 110.

In particular embodiments, the linear interlocking mechanism can be a pin. In particular, a pin 150 is located between a hole 152 in the wall of the separate compartment 110 and the housing 102 of the device 100, preventing the separate compartment 110 from being released. At a particular condition and/or predetermined time, the pin 150 is either pulled inwards or pushed outwards, allowing the separate compartment 110 to be released. FIG. 8E shows an embodiment wherein retention means 112 comprises a pin 150 as a linear interlocking mechanism.

In particular embodiments, the linear interlocking mechanism is a bi-metallic latch. In particular, a shaped bi-metallic latch 156 is fixed to the outer surface of the housing 102, such that one end protrudes through a hole 154 in the housing 102 and into a hole 152 in the separate compartment 110. At a particular condition and/or predetermined time, the bi-metallic latch 156 is heated and thereby deforms, causing the protruding end of latch 156 to retreat and allowing the separate compartment 110 to be released. FIG. 8F shows an embodiment wherein retention means 112 comprises a bi-metallic latch as a linear interlocking mechanism.

In particular embodiments, the linear interlocking mechanism can be electromagnets. In particular, the end surface 174 of the separate compartment 110 consists of a ferrous material. The end 176 of the housing 102 is made from a ferrous electromagnet. A current is passed through the electromagnet, generating an attractive force between the end 176 of the housing 102 and the end surface 174 of the separate compartment 110, preventing the separate compartment 110 from being released. When the current is removed, the attractive force no longer exists and the separate compartment 110 can be released. FIG. 8J an embodiment wherein retention means 112 comprises electromagnets as a linear interlocking mechanism.

In yet other embodiments, the retention means 112 can be a fastening means and/or a material that reacts to changes in the external environment of the device 100 (as previously described). In particular, the actuation means 108 of the device 100 is tethered 116 to a closure means 118 and wherein the movement of the actuation means 108 results in the closure means 118 blocking the opening 106. In other embodiments, the fastening means is also tethered 116 to the closure means 118. Such an embodiment is shown in FIG. 7.

A fastening means can be any device or coupled elements, which can hold and secure other objects to prevent movement or separation through the application of pressure.

In particular, the fastening means can be a clamp which holds the tether 116 in place under tension.

In particular embodiments, the fastening means can be activated by any form of interlocking mechanism previously described. The interlocking mechanism may be fastened or released by rotary, radial or linear motion or means. Preferably, the interlocking mechanism is a catch. Any form of catch known in the art can be used.

The catch may consist of a number of parts that are caused to interfere with each other, possibly in association with levers and pivot points. The parts may include hook elements and/or friction elements. One part of this grouping can be flexible, such that when a force is applied to it, it bends or deforms or otherwise moves. This movement is arranged such that the constituent parts of the catch no longer interfere with each other and the catch is released, thereby releasing the retention means and thus releasing the separate compartment 110.

In this particular embodiment, the actuation means 108 may not comprise a spring, may not comprise a valve and may not comprise a stopper means.

As is shown in FIG. 7, the actuation means 108 (e.g. the plunger/piston 108A) and the closure means 118 are tethered. When the retention means 112 (either the fastening means and/or the material that reacts to changes in the external environment of the device) is activated (passively or actively), the separate compartment 110 is released, thereby the actuation means 108 moves along the housing 102 of the sampling device 100 due to a pressure drop within the housing 102 of the device 100. The actuation means 108 is tethered with the closure means 118 and is under tension. The actuation means 108 moves along the housing 102 of the device 100, and the tensed tether 116 pulls the closure means 118 along until the closure means 118 reaches the opening 106. The closure means 118 is pushed or pulled into the opening 106, forming a closed device 100. Simultaneously, the actuation means 108 draws up sample into the chamber 104 of the device 100. Thereby, the sample is sealed within the device 100. As the actuation means 108 is tethered to the closure means 106 under tension, the actuation means 108 (plunger/piston) cannot be released further and thus a stopper means is not required to stop the plunger 108B from exiting from the device 100.

In alternative embodiments, the retention means 112 is also tethered to the closure means 118 under tension.

Further embodiments, may comprise a spring 108A to increase the force in which the actuation means 108 drives along the housing.

Figure 6:
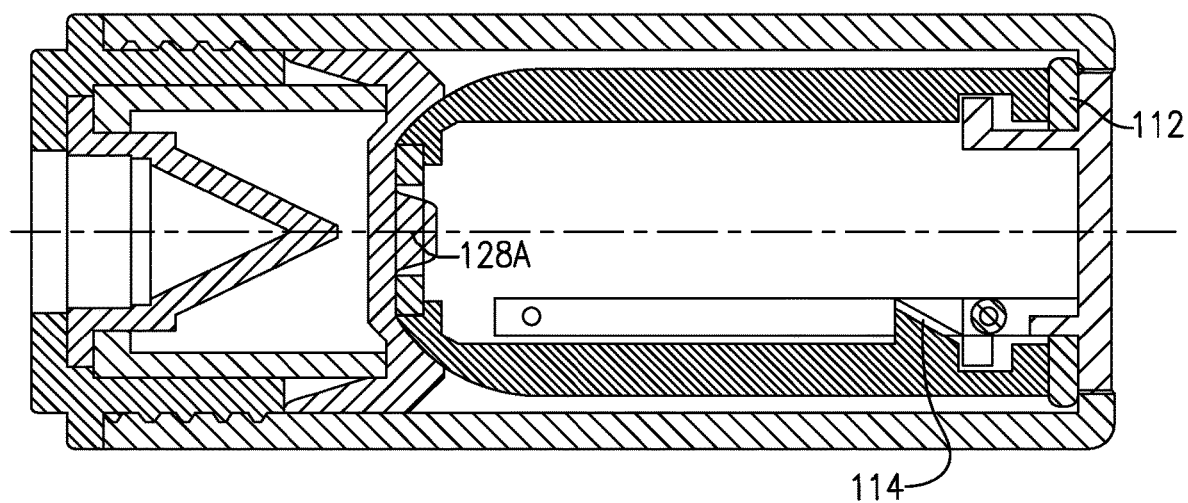
FIG. 6 is a cross-sectional view of a sampling device incorporating another embodiment of a retention means.

As shown in FIGS. 5-7, The sampling device 100 may further comprise a trigger means 114. The trigger means 114 can be an element of the device 100, which can be activated automatically, pre-programmed and/or activated remotely. A trigger means 114 can be an element which is capable of interaction with the retention means 112 to provide the effect to release the separate compartment 110 of the sampling device 100.

In particular embodiments, the retention means 112 can be activated by a trigger means 114 and/or in response to a release parameter.

In particular embodiments, the interlocking mechanism can be activated by a trigger means 114 and/or in response to a release parameter.

In particular embodiments, the fastening means can be activated by a trigger means 114 and/or in response to a release parameter.

In particular, the trigger means 114 can be activated automatically, preprogrammed and/or activated remotely.

In some embodiments, the trigger means 114 may be a form of electronic actuation.

Electronic actuation can be selected from electro-magnetic means (such as solenoids and/or motor, magnetostrictive materials), piezo-electronic means (such a stack or diaphragm), shape changers (muscle wire), electro-chemical (battery gassing, spark generator, light sensitive adhesive), heating element and/or fusing (fuse blowing, heating element or wax actuator).

In particular embodiments, the trigger means 114 can be a solenoid or a motor. The solenoid or motor may consist of a wire coiled around a central metallic core. When a current is passed through the wire, the resulting electromagnetic field causes the solid core to move. This movement can be utilized to affect one or more of the mechanisms required to release the interlocking mechanism and/or retention means 112.

In particular embodiments, the trigger means 114 can be a magnetorestrictive material. When a magnetic field is applied to the magnetorestrictive material, the material changes shape and/or dimension. This change in shape or dimension can be utilized as a kinetic energy source to affect one or more of the mechanisms required to release the interlocking mechanism and/or retention means.

In particular embodiments, the trigger means 114 can be a piezomagnetic material. When an electrical field is applied to a piezomagnetic material there is a resulting mechanical strain. The force produced by this piezoelectric effect can be utilized as a kinetic energy source to affect one or more of the mechanisms required to release the interlocking mechanism and/or retention means 112. The available force may be multiplied by stacking piezo electric elements.

In particular embodiments, the trigger means 114 can be a muscle wire. In particular, a muscle wire can be a fibre of nickel-titanium alloy (e.g. Nitinol® or Flexinol®) that changes length in the presence of an electric current. The force generated by this change in length can be utilized as a kinetic energy source to affect one or more of the mechanisms required to release the interlocking mechanism and/or retention means 112.

In particular embodiments, the trigger means 114 can be a fuse. In particular, a length of material is used to withhold the energy of the actuation means 108 (e.g. comprising a spring), preventing the separate compartment 110 from being released form the housing 102 of the device 100. When a current is applied to the material, electrical resistance causes the material to heat up and mechanically fail. Typically, the material would be zinc, copper, silver, aluminum or alloys designed to provide a predictable failure characteristic. Failure of the fuse would release the interlocking mechanism and/or retention means 112 allowing the separate compartment 110 to be released.

In further embodiments, the retention means 112 and/or the trigger means 114 can be activated automatically, pre-programmed and/or activated remotely.

The trigger means 114 may be initiated automatically in response to a release parameter (pH, temp, etc.). The trigger means 114 can be initiated by instructions programmed into the microprocessor 128D of the separate compartment 110 in response to a release parameter. The trigger means 114 can also be initiated by an external wireless system in response to an external release parameter e.g. time, daylight, or through direct intervention by a user of the device 100.

In some embodiments, the retention means 112 and/or the trigger means 114 are activated in response to a release parameter. In particular embodiments, the retention means 112 is released in response to a release parameter.

When the retention means 112 can be activated by physiological characteristics, such as pH, pressure, temperature, or external remote activation, the release parameter may activate the retention means 112 and/or trigger means 114.

A release parameter can be a change in pH, a change in temperature, a change in light, a change in moisture, solute concentration and/or enzyme activity or concentration and/or can be activated at a predetermined time and/or at a predetermined pH and/or at a predetermined temperature and/or predetermined light, and/or predetermined moisture and/or predetermined solute concentration and/or predetermined enzyme activity or concentration or location and/or environmental conditions, etc.

In particular embodiments, the retention means 112 can be activated remotely from outside the body of the animal, or can be pre-programmed based on time, or can be activated based on other physiological characteristics, such as pH, pressure, temperature, etc.

In particular, the retention means 112 may be responsive to the external environment of the device 100 and/or activated in response to a predetermined signal from the internal processor and/or controller in the device 100.

The device 100 can be programmed to open relative to a pH signal that signifies gastric emptying, for example, 60 minutes after pH increases above pH3 or 60 minutes after pH has risen for at least 2 pH units and remained elevated for 3 consecutive minutes. Additionally, the change in temperature can also be useful to identify elevations in gastric pH due to ingestion of water, so that these instances are not mistaken for gastric emptying.

Calibration techniques using parameters such as time, temperature, pH, etc. to determine location in the gastrointestinal tract of an animal are known in the art. In general, the pH during transit in the gastrointestinal tract would be expected to rise sharply on gastric emptying, continue to rise at a slower rate along the small intestine, drop sharply on entering the large intestine, before starting to rise again very slowly (this can be seen in FIG. 9). In particular, the timing at which the device 100 reaches the end of the small intestine may be identified, for example, as follows; (1) detecting a rise in pH of at least 4 pH units, (2) such rise in pH persists for about 10 minutes and (3) such rise is at least 30 minutes after exiting the stomach.

In some embodiments, the device 100 may include a controller (internally or externally from the device) which controls the activation of the retention means 112. In particular, the controller may either generate a signal at a predetermined time or may receive a signal externally or generate a signal in response to sensed parameters, such as pH, temperature, pressure, enzyme activity, or the like.

In some embodiments, a signal is induced in the circuit of the device 100 by an array of electromagnetic coils external to the body of the test subject. Movement of the test subject, (for example by walking between the array of electromagnetic coils, or by moving a handheld coil array around the body of the test subject), induces a current in the circuit of the device 100. This current is interpreted as a signal that functions as a release parameter.

In some embodiments, the circuit contains a signal receiving coil that receives a wireless signal from an external transmitter. This signal can be initiated at any time by an external operator and functions as the release parameter.

In particular specific embodiments of the invention, the retention means 112 can be a rotary interlocking mechanism, such as bayonet mount, that is activated by a trigger means 114. FIGS. 5A and 5B are schematic illustrations of an example of a bayonet mount as a rotary interlocking mechanism on the device 100.

In specific embodiments of the invention, the retention means 112 can be a rotary interlocking mechanism, such as a bayonet mount, that is activated by a trigger means 114, such as a piezo beam.

In particular, the separate compartment 110 is inserted into the housing 102 and is rotated to engage with the actuation means 108. The separate compartment 110 and the actuation means 108 (i.e. plunger/piston 108B) engage with each other in order to maintain a stored energy by means of a pin or other locating device. This rotation causes a spring 108A in the interlocking mechanism, which provides the force to rotate the separate compartment 110 within the housing 102, to be extended, storing an amount of energy within the spring 108A. The rotation also causes protrusions on the separate compartment 110 and housing 102 to be aligned, preventing the separate compartment 110 from being released and thereby releasably retained. The device 100 is thereby in its compressed configuration.

When the sensors (e.g. pH 128B and/or temperature) detect an appropriate change in pH and/or temperature, a signal is sent from the microprocessor to a piezo electric beam, causing the beam to be deflected. This deflection disengages the locating pin and allows the stored spring energy to be released, rotating the separate compartment 110 within the housing 102. This rotation misaligns the protrusions in the separate compartment 110 and the housing 102, allowing the separate compartment 110 to be ejected by the actuation means 108.

In specific embodiments of the invention, the retention means 112 can be a rotary interlocking mechanism, such as a bayonet mount, that is activated by a trigger means 114, such as a muscle wire.

In particular, the separate compartment 110 is inserted into the housing 102 and is rotated to engage with the actuation means 108 by a pin or other locating device. This rotation causes a spring to be extended, storing an amount of energy within the spring. The rotation also causes protrusions on the separate compartment 110 and housing 102 to be aligned, preventing the separate compartment 110 from being released. The device is now in its compressed state. When the sensors (e.g. pH 128A and/or temperature) detect an appropriate change in pH and/or temperature, a signal is sent from the microprocessor to a length of muscle wire, causing the muscle wire to shorten. One end of the muscle wire is attached to the locating pin. This shortening disengages the locating pin and allows the stored spring energy to be released, rotating the separate compartment 110 within the housing 102. This rotation misaligns the protrusions in the separate compartment 110 and the housing 102, allowing the separate compartment 110 to be ejected by the actuation means 108.

In specific embodiments of the invention, the retention means 112 can be a rotary interlocking mechanism, such as a bayonet mount, that is activated by a trigger means 114, such as a shape memory alloy (SMA)

In particular, the separate compartment 110 is inserted into the housing 102 and is rotated to engage with the actuation means 108 by a pin or other locating device. This rotation causes a simple spring element to be extended, storing an amount of energy within the spring. The rotation also causes protrusions on the separate compartment 110 and housing 102 to be aligned, preventing the separate compartment 110 from being released. The device 100 is now in its compressed state. When the sensors (e.g. pH 128A and/or temperature) detect an appropriate change in pH and/or temperature, a signal is sent from the microprocessor to a length of deformed shape memory alloy, causing the shape memory alloy to revert to its initial form. One end of the shape memory alloy is attached to the locating pin. This change in form disengages the locating pin and allows the stored spring energy to be released, rotating the separate compartment 110 within the housing 102. This rotation misaligns the protrusions in the separate compartment 110 and the housing 102, allowing the separate compartment 110 to be ejected by the actuation means 108.

In particular specific embodiments of the invention, the retention means 112 can be a radial interlocking mechanism, such as compressible material that is activated by a trigger means 114. FIG. 6 is a schematic illustration of an example of an O-ring as a radial interlocking mechanism on the device.

In specific embodiments of the invention, the retention means 112 can be a radial interlocking mechanism, such as a compressible material in the form of an O-ring, that is activated by the trigger means 114 such a piezo beam.

In particular, the separate compartment 110 is inserted linearly into the housing 102. Continuing linear force on the separate compartment 110 (after it is inside the housing 102) causes an elastic O-ring to be compressed between the cap 110B and body 110A of the separate compartment 110. This compression causes deformation of the O-ring, such that it interferes with a stopper means 122 (e.g. lip) on the end of the housing 102, preventing the separate compartment 110 from being released. The O-ring is kept in compression by a catch mechanism within the separate compartment 110. When the sensors (e.g. pH 128A and/or temperature) detect an appropriate change in pH and/or temperature, a signal is sent from the microprocessor to a piezo electric beam, causing the beam to be deflected. This deflection disengages the catch mechanism and allows the O-ring to be restored to its initial, decompressed state in which it no longer interferes with the stopper means (e.g. lip 122) on the housing 102. The separate compartment 110 is then ejected by the actuation means 108.

In specific embodiments of the invention, the retention means 112 can be a radial interlocking mechanism, such as a compressible material in the form of an O ring, that is activated by the trigger means 114 such a muscle wire.

In particular, the separate compartment 110 is inserted linearly into the housing 102. Continuing linear force on the separate compartment (after it is inside the housing 102) causes an elastic O-ring to be compressed between the cap 110B and body 110A of the separate compartment 110. This compression causes deformation of the O-ring such that it interferes with a lip 122 on the end of the housing 102, preventing the separate compartment 110 from being ejected. The O-ring is kept in compression by a catch mechanism within the separate compartment 110. When the sensors (e.g. pH 128A and/or temperature) detect an appropriate change in pH and/or temperature a signal is sent from the microprocessor to a length of muscle wire, causing the muscle wire to shorten. One end of the muscle wire is attached to the catch mechanism. This shortening disengages the catch mechanism and allows the O-ring to be restored to its initial, decompressed state in which it no longer interferes with the lip 122 on the housing 102. The separate compartment 110 is then free to be ejected by the actuation means 108.

In specific embodiments of the invention, the retention means can be a radial interlocking mechanism, such as a compressible material in the form of an O-ring that is activated by the trigger means such a Shape Memory Alloy (SMA).

In particular, the separate compartment 110 is inserted linearly into the housing 102. Continuing linear force on the separate compartment 110 (after it is inside the housing 102) causes an elastic O-ring to be compressed between the cap 110B and body 110A of the separate compartment 110. This compression causes deformation of the O-ring, such that it interferes with a stopper means (e.g. lip 122) on the end of the housing 102, preventing the separate compartment 110 from being released. The O-ring is kept in compression by a catch mechanism within the separate compartment 110. When the sensors (e.g. pH 128A and/or temperature) detect an appropriate change in pH and/or temperature, a signal is sent from the microprocessor to a length of deformed shape memory alloy, causing the shape memory alloy to revert to its initial form. One end of the shape memory alloy is attached to the catch mechanism. This change in form disengages the catch mechanism and allows the O-ring to be restored to its initial, decompressed state in which it no longer interferes with the stopper means 122 on the housing 102. The separate compartment 110 is then free to be ejected by the actuation means 108.

In particular, specific embodiment of the invention, the retention means 112 can be a fastening means that is activated by a trigger means 114. FIG. 7 is a schematic representation of an example of a fastening means as a retention means of the device.

In specific embodiments of the invention, the retention means 112 can be a fastening means that is activated by a trigger means 114, such as a piezo beam.

In particular, the separate compartment 110 is inserted linearly into the housing 102, causing the actuation means 108 to be compressed. A tether 116 is attached to the actuation means 108 and extends around the outer surface of the device 100 and is gripped in by the fastening retention means (such as a clamping mechanism). The fastening means consists of a protrusion extending through a membrane on the surface of the separate compartment 110. The protrusion is held in position by a latch and lever mechanism inside the separate compartment 110. The latch may be initially engaged by the temporary action of a magnet or electromagnet. The fastening means allows the tie to be kept under tension, thereby preventing movement of the actuation means 108. When the sensors (e.g. pH 128A and/or temperature) detect an appropriate change in pH and/or temperature, a signal is sent from the microprocessor to a piezo electric beam, causing the beam to be deflected. This deflection disengages the catch and lever mechanism and allows the fastening means to release. The actuation means 108 is then free to push and eject the separate compartment 110. As the actuation means 108 travels along the housing 102, the tether 116 is drawn though the opening 106. A closure means 118 is attached at a point on the tether 116 that serves to block the opening 106 of the device 100, when the actuation means 108 is completely extended.

In specific embodiments of the invention, the retention means 112 can be a fastening means that is activated by a trigger means 114, such as a muscle wire.

In particular, the separate compartment 110 is inserted linearly into the housing 102, causing the actuation means 108 to be compressed. A tether 116 is attached to the actuation means 108 and extends around the outer surface of the device 100 to be gripped by a fastening retention means (such as a clamping mechanism). The fastening means consists of a protrusion extending through a membrane on the surface of the separate compartment 110. The protrusion is held in position by a latch and lever mechanism inside the separate compartment 110. The catch may be engaged by the temporary action of a magnet or electromagnet. The fastening means allows the tether 116 to be kept under tension, thereby preventing movement of the actuation means 108. When the sensors (e.g. pH 128A and/or temperature) detect an appropriate change in pH and/or temperature, a signal is sent from the microprocessor to a length of muscle wire, causing the muscle wire to shorten. One end of the muscle wire is attached to the catch and lever mechanism. This shortening disengages the catch and lever mechanism and allows the fastening means to release. The actuation means 108 is then free to eject the separate compartment 110. As the actuation means 108 travels along the housing, the tether 116 is drawn though the opening 106 of the device 100. A closure means 118 is attached at a point on the tether 116 that serves to block the opening 106 of the device 100 when the actuation means 108 is completely extended.

In specific embodiments of the invention, the retention means 112 can be a fastening means that is activated by a trigger means 114, such as a Shape Memory Alloy (SMA).

In particular, the separate compartment 110 is inserted linearly into the housing 102, causing the actuation means 108 to be compressed. A tether 116 is attached to the actuation means 108 and extends around the outer surface of the device 100 to be gripped by a fastening retention means (such as a clamping mechanism). The fastening means consists of a protrusion extending through a membrane on the surface of the separate compartment. The protrusion is held in position by a latch and lever mechanism inside the separate compartment. The catch may be engaged by the temporary action of a magnet or electromagnet. The fastening means allows the tether 116 to be kept under tension, thereby preventing movement of the actuation means 108. When the sensors (e.g. pH 128A and/or temperature) detect an appropriate change in pH and/or temperature, a signal is sent from the microprocessor to a length of deformed shape memory alloy, causing the shape memory alloy to revert to its initial form. One end of the shape memory alloy is attached to the catch and lever mechanism. This change in form disengages the catch and lever mechanism and allows the fastening means to release. The actuation means 108 is then free to eject the separate compartment 110. As the actuation means 108 travels along the housing 102, the tether 116 is drawn though opening 106 of the device 100. A closure means 118 is attached at a point on the tether 116 that serves to block the opening 106 of the device 100, when the actuation means 108 is completely extended.

A second aspect of the invention provides a method of obtaining a sample (e.g. internal substance from the gastrointestinal tract of an animal), comprising the following steps; orally administering the device 100 of the invention to the animal, and recovering the device 100 and/or separate compartment 110.

The device 100 can be orally ingested by the animal, recovered from the stool and the sample within the device 100 easily extracted. The sample is preserved and recovered from the device 100 to perform various biological, chemical and physical tests, such as total nitrogen tests for protein, amino acid analysis using high performance liquid chromatography, measuring the size of the peptides, for example by gel permeation chromatography, assessing immune factors present such as by ELISA, identification, enumeration of microbes using microbiological culture methods or molecular/DNA sequencing or fingerprint analysis or detection of metabolites for example by Mass spectrometry.

In some embodiments, the device 100 can be administered to the animal in a fasting state, with food or at an interval before and/or after feeding.

In some embodiments, more than one sampling device 100 can be ingested by the animal. Each device 100 may be ingested by the animal at different times. Each device 100 is capable of taking separate samples at different points along the gastrointestinal tract. The sampling devices 100 may be ingested separately and/or are coupled together.

In particular, the sampling device 100 can store and/or obtain a volume of up to about 18 to 20 ml depending on the size of the device 100.

In some embodiments, the method of the invention is carried out on an animal, for example a mammal. The animal may be a human and/or a companion animal, farm animal or production animal, such as a dog, cat, horse, cow, sheep and/or a chicken.

Modifications to the device 100 may be necessary according to the species on which it is used. In particular, smaller devices would be required for smaller animals. Differences in gastrointestinal pH-profile also need to be accounted for, in particular in the case of ruminants.

Methods of detecting the device 100 during its transit along the gastrointestinal tract of an animal are readily known in the art, such as the use of radiography or ultrasound. Other modes of detecting the device 100, such as inserting a microchip and/or wireless transmission are readily known in the art.

The device 100 can be used in any method where intervention (human or other) is preferably or necessarily avoided. Such methods include taking a sample from processing tanks (for example sewage, food and beverages, manufacture of biologics or chemicals, such as fuels, agricultural systems, for example biofuels or fertilizer and pesticide production, fish tanks (household or industrial) hospital or factory pipes. The method involves adding the device 100 to the system described above and ultimately obtaining the device 100 and/or separate compartment 110 from the system. The device 100 and/or separate compartment 110 may be retrieved from the same location or from a different location in the system. The device 100 and/or separate compartment 110 may have travelled through the system before it is retrieved.

The invention will now be further described by way of reference to the following Example which is provided for the purpose of illustration only and is not to be construed as being limiting on the invention.

The separate compartment 110 is removed from the device 100 and unscrewed to allow access to the onboard electronics. The microprocessor 128E is connected to a serial communications clip to allow configuration of an appropriate sample rate. A new battery 120 is inserted onto the printed circuit board and the separate compartment 110 is then resealed. The electronics record pH data from the point of battery 120 insertion until the battery 120 is removed. Each sampling event is associated with a flash of the LED to indicate to the user that the device 100 is functioning correctly.

The pH sensor 128A is then calibrated against a known set of pH buffer solutions.

The separate compartment 110 is inserted into the housing 102 along with a washer made of a material that degrades in alkaline pH conditions. This washer acts as a retention means 112, preventing the separate compartment 110 from being ejected.

The valve assembly 126, 106 is screwed into the housing 102. This compresses the spring 108A of the actuation means 108, forcing the plunger 108B against the separate compartment 110. A protrusion 108D on the plunger 108B engages with the switch assembly 128A on the printed circuit board through a membrane on the surface of the separate compartment 110. This is recorded by the onboard electronics as indicating that the device 100 is in its closed/compressed configuration.

The device 100 is then ready to be administered to the test subject.

During transit along the gastrointestinal tract, the device 100 samples the output of the pH sensor 128A according to the predetermined sampling rate, for example, every 30 seconds. On exit from the stomach, the washer of the retention means 112 begins to degrade in the alkaline environment of the duodenum. When the washer 112 has degraded to such an extent that it is no longer able to withstand the force of the compressed spring 108A of the actuation means 108, the separate compartment 110 is ejected from the device 100.

As the separate compartment 110 is ejected from the device 100, the movement of the plunger 108O along the length of the device 100 creates a temporary vacuum that draws a sample of digestive tract contents into the device 100 through an opening 106. During this time, the pressure of the plunger protrusion 108D on the switch assembly 128A is reduced. This is recorded by the onboard electronics as indicating that the device 100 is in its open/uncompressed configuration.

Following transit through the entire digestive tract, the device 100 and/or separate compartment 110 is recovered on elimination. The device 100 is recovered in two parts. The compartment which contains the sampled digestive tract contents and the separate compartment 110 containing the data relating to the pH recorded during transit and record of the time of sampling represented by the change in the condition of the switch 128A.

The device 100 is unscrewed to retrieve the sampled digestive tract contents. The separate compartment 110 undergoes a second calibration against a known set of pH buffer solutions to check for drift in the output of the pH sensor 128A compared to the initial calibration.

The separate compartment 110 is unscrewed and the battery 120 removed. Data is downloaded from the onboard flash memory 128H through a serial communications clip 128G attached to the microprocessor 128E. This data can be seen in FIG. 9.

The device 100 is reprogrammed and ready to use again.

Figure 9:
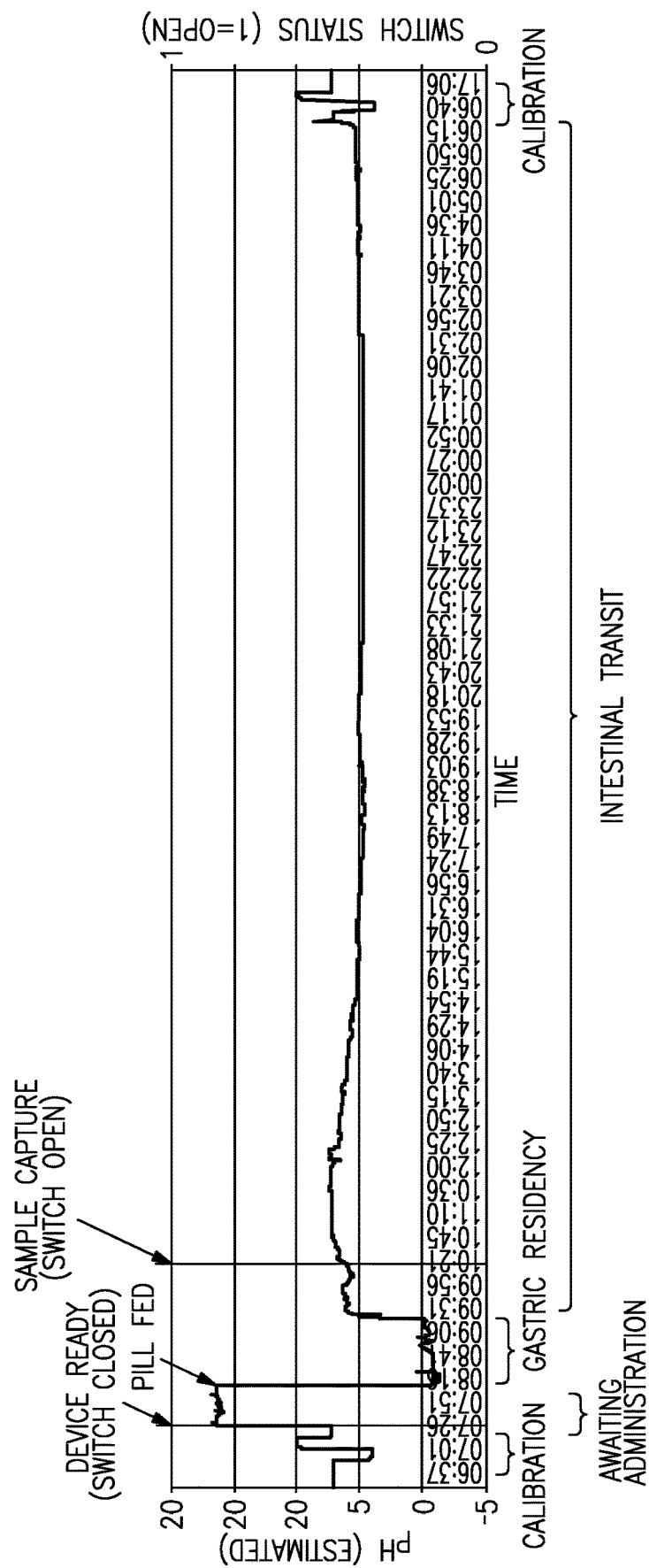
FIG. 9 is a plot of data obtained by one embodiment of the sampling device from the gastrointestinal tract of an animal.

The results in FIG. 9 show the pH calibration along the gastrointestinal tract of the animal, at which point the sample was captured, and the corresponding pH.

The invention claimed is:

1. A sampling device for collection of a sample from within a human or animal body comprising a housing, the housing comprising a chamber, at least an opening, an actuation means and a separate compartment, wherein:
   the separate compartment is an enclosed, water-tight compartment, releasably retained within the housing by a retention means configured for external control from outside the body of the human or animal; and
   wherein the actuation means enables the sample to be drawn in through the opening into the chamber and simultaneously pushes the separate compartment along the housing until the separate compartment is ejected from the housing of the sampling device, thereby creating an increased space or volume for receiving and storing the sample within the chamber of the sampling device.

2. The sampling device of claim 1, wherein the opening is a one way valve.

3. The sampling device of claim 1, wherein the actuation means comprises at least a plunger.

4. The sampling device of claim 3, wherein the actuation means is a spring and a plunger arrangement.

5. The sampling device of claim 1, wherein the actuation means is coupled at one end of the housing of the sampling device and the separate compartment is releasably retained by the retention means within the housing at the opposing end of the sampling device.

6. The sampling device of claim 1, wherein when the retention means is activated, the separate compartment is at least partially released and at least partly disengaged from the housing.

7. The sampling device of claim 1, wherein the device is reusable.

8. The sampling device of claim 1, wherein the retention means further comprises an interlocking mechanism between the housing and the separate compartment.

9. The sampling device of claim 8, wherein the interlocking mechanism is fastened and/or released by a rotatory, radial or linear motion or means.

10. The sampling device of claim 9, wherein the rotatory interlocking mechanism is a bayonet mount.

11. The sampling device of claim 9, wherein the interlocking mechanism is a rubber O-ring washer.

12. The sampling device of claim 9, wherein the interlocking mechanism is a pin that pushes the separate compartment into place.

13. The sampling device of claim 8, wherein the interlocking mechanism is activated by a trigger means selected from an electromagnetic or piezoelectric means, a shape memory alloy, muscle wire or a sacrificial fuse.

14. The sampling device of claim 13, wherein the interlocking mechanism is a bayonet mount that is activated by the trigger means.

15. The sampling device of claim 13, wherein the interlocking mechanism is a rubber O-ring washer that is activated by the trigger means.

16. The sampling device of claim 13, wherein the interlocking mechanism and/or the trigger means are activated automatically, pre-programmed and/or activated remotely.

17. The sampling device of claim 16, wherein the interlocking mechanism and/or trigger means is/are activated in response to pH, temperature, moisture, solute concentration, enzyme concentration, light, time or a combination of these.

18. The sampling device of claim 1, wherein the separate compartment comprises a battery, and one or both of a sensor and a microprocessor.

* * * * *